United States Patent
Shepard et al.

(10) Patent No.: US 9,938,566 B2
(45) Date of Patent: Apr. 10, 2018

(54) PROFILING EXPRESSION AT TRANSCRIPTOME SCALE

(71) Applicants: Peter J. Shepard, Carlsbad, CA (US); Joanne M. Yeakley, Encinitas, CA (US); Bruce Seligmann, Tuscon, AZ (US)

(72) Inventors: Peter J. Shepard, Carlsbad, CA (US); Joanne M. Yeakley, Encinitas, CA (US); Bruce Seligmann, Tuscon, AZ (US)

(73) Assignee: BioSpyder Technologies, Inc., Rancho Santa Fe, CA (US)

( * ) Notice: Subject to any disclaimer, the term of this patent is extended or adjusted under 35 U.S.C. 154(b) by 457 days.

(21) Appl. No.: 14/595,069

(22) Filed: Jan. 12, 2015

(65) Prior Publication Data

US 2016/0068907 A1   Mar. 10, 2016

Related U.S. Application Data

(63) Continuation-in-part of application No. 14/480,525, filed on Sep. 8, 2014.

(51) Int. Cl.
C12Q 1/68       (2018.01)

(52) U.S. Cl.
CPC ................. *C12Q 1/6813* (2013.01)

(58) Field of Classification Search
None
See application file for complete search history.

(56) References Cited

U.S. PATENT DOCUMENTS

| | | |
|---|---|---|
| 6,812,005 B2 | 11/2004 | Fan |
| 7,361,488 B2 | 4/2008 | Fan |
| 7,582,420 B2 | 9/2009 | Oliphant |
| 8,150,627 B2 | 4/2012 | Fan |
| 8,188,265 B2 | 5/2012 | Costa |
| 8,288,103 B2 | 10/2012 | Oliphant |
| 2011/0045462 A1 | 2/2011 | Fu |
| 2012/0302451 A1 | 11/2012 | Fu |
| 2013/0244882 A1 | 9/2013 | Oliphant |

OTHER PUBLICATIONS

Li et al., "RASL-seq for Massively Parallel and Quantitative Analysis of Gene Expression," Curr. Protoc. Mol. Biol. 2012, 98:4.13.1-4.13.9.*
Gerhold, "RASL-Seq: A Gene Expression Platform . . . " NCATS presentation (Mar. 20, 2014).
Lalonde et al., "Sensitive Oligonucleotide Ligation Assay for Low-Level Detection . . . " J. Clin. Microb. 45:2604-2615 (Aug. 2007).
Nilsson et al., "RNA-templated DNA ligation for transcript analysis" Nucleic Acids Research 29:578-581 (2001).
Larman et al., "Sensitive, multiplex and direct quantification of RNA sequences using a modified RASL assay" Nucleic Acids Research Advance Access (Jul. 25, 2014).
Li et al., "RASL-seq for Massively Parallel and Quantitative Analysis of Gene Expression," Curr. Protocols in Mol. Bio. 4.13. 1-4.13.9 (Apr. 2012).
Li et al., "Determination of tag density required for digital transcriptome analysis . . . " PNAS 105:20179-20184 (Dec. 23, 2008).
Li et al., "Versatile pathway-centric approach based on high-throughput sequencing . . . " PNAS 109:4609-4614 (Mar. 20, 2012).
Wang et al., "Timing of plant immune responses by a central circadian regulator," Nature 470:110-115 (Feb. 3, 2011).
Zhou et al., "The Akt-SRPK-SR Axis . . . " Molecular Cell 47:422-433 (Aug. 10, 2012).

* cited by examiner

*Primary Examiner* — Kaijiang Zhang

(57) ABSTRACT

Ligation assays for detecting and profiling expression products at transcriptome scale.

22 Claims, 17 Drawing Sheets

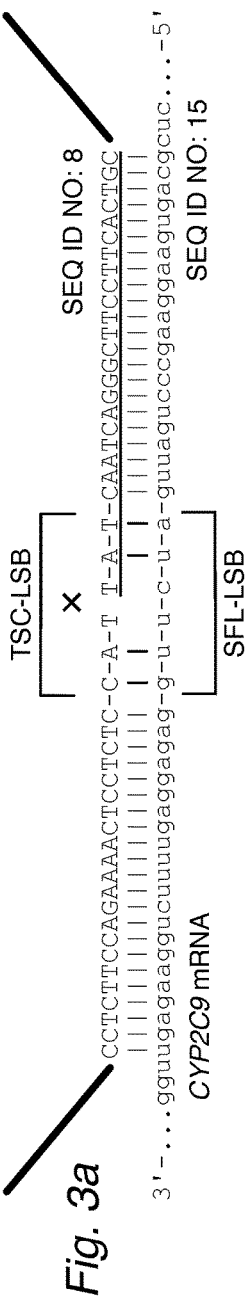
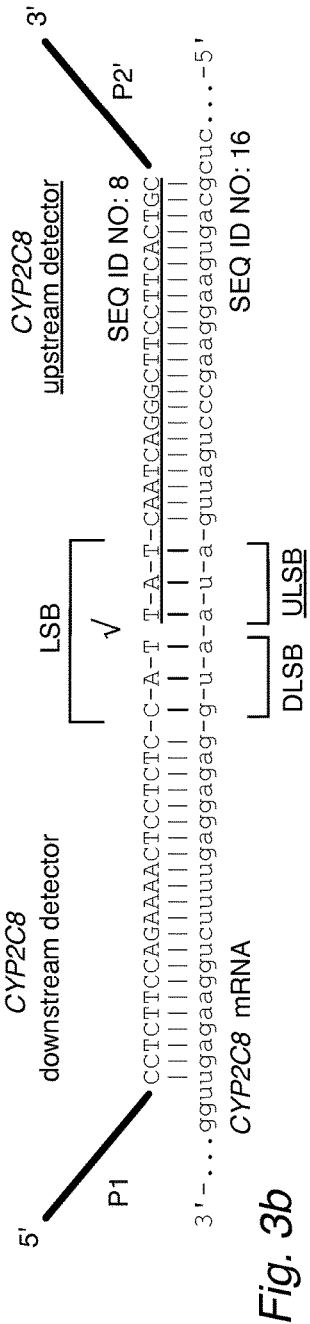
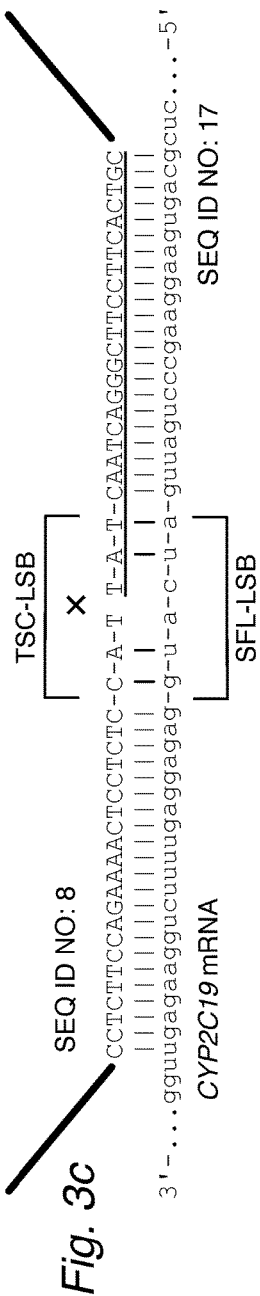
Fig. 3a
Fig. 3b
Fig. 3c

Fig. 3d

```
                         TSC-LSB
                         ┌─────┐
     CCTCTTCCAGAAAACTCCTCT-C-C-A-T  T-ATCAATCAGGGCTTCCTTCACTGC          SEQ ID NO: 8
     ||||||||||||||||||||| X        ||||||||||||||||||||||||||
3'-...gguugaaggucuuuugaggaga-g-u-u-c-uaguuaggucccgaaggaagugacgcuc...-5'  SEQ ID NO: 15
                           └──┬──┘
                            DLSB  ULSB
     CYP2C9 mRNA
```

Fig. 3e

```
                         TSC-LSB
                         ┌─────┐
     CCTCTTCCAGAAAACTCCTCTC        T-A-T-CAATCAGGGCTTCCTTCACTGC          SEQ ID NO: 8
     |||||||||||||||||||||  ↑↑ ✓   ||||||||||||||||||||||||||
3'-...gguugaaggucuuuugaggagag-u-a-u-a-guuagucccgaaggaagugacgcuc...-5'   SEQ ID NO: 16
                                      └─┬─┘
                                       ULSB
     CYP2C8 mRNA
```

Fig. 3f

```
                         TSC-LSB
                         ┌─────┐
     CCTCTTCCAGAAAACTCCTCTC=C=A=T  T=A=T=CAATCAGGGCTTCCTTCACTGC          SEQ ID NO: 8
     |||||||||||||||||||||  X      ||||||||||||||||||||||||||
3'-...gguugaaggucuuuugaggagag-u-a-c-u-a-guuagucccgaaggaagugacgcuc...-5' SEQ ID NO: 17
     CYP2C19 mRNA
```

Fig. 4a: patterns of X

| NM pos. | match pattern | | match score (Fig.) | | |
|---|---|---|---|---|---|
| | | | 5a | 5b | 5c |
| 1175-1126 | IIIIIX | 5'- DR'.........NNNNNN.........UR'<br>5'- GTCACTGTATCTCTGGATCTCGTGCACTACAGCATCAGTGTAAGGCATGT | 0.1 | 0.1 | 0.1 |
| 1174-1125 | IIIIXI | 5'- TCACTGTATCTCTGGATCTCGTGCACTACAGCATCAGTGTAAGGCATGTG | 0.1 | 0.1 | 0.1 |
| 1173-1124 | IIIXII | 5'- CACTGTATCTCTGGATCTCGTGCACTACAGCATCAGTGTAAGGCATGTGG | 0.4 | 0.4 | 0.4 |
| 1172-1123 | IIXIII | 5'- ACTGTATCTCTGGATCTCGTGCACTACAGCATCAGTGTAAGGCATGTGGC | 0.4 | 0.4 | 0.4 |
| 1171-1122 | IXIIII | 5'- CTGTATCTCTGGATCTCGTGCACTACAGCATCAGTGTAAGGCATGTGGCT | 0.4 | 0.4 | 0.1 |
| 1170-1121 | XIIIII | 5'- TGTATCTCTGGATCTCGTGCACTACAGCATCAGTGTAAGGCATGTGGCTC | 0.1 | 0.1 | 0.1 |
| 1175-1121 | CYP2C8 cDNA | 5'- GTCACTGTATCTCTGGATCTCGTGCACTACAGCATCAGTGTAAGGCATGTGGCTC<br>       ||||||||||||||||||||||||||||||||||||||||||||||||||||||| | SEQ ID NO: 8 | | |
| 1175-1121 | CYP2C8 mRNA | 3'- cagugacauagagaccuggagcacgugaugucguagacacauccguacaccgag | SEQ ID NO: 8 | | |
| 1105-1016 | SFL CYP2C9 | ||||  |||||||||||||||||||||||  |||||| X|  |||||||||  |||||||||||||||| |<br>3'- caguuacauagagaccuggagcacgugguguguuagacacauccguacaccgag | SEQ ID NO: 9 | | |
| 1406-1352 | SFL CYP2C18 | |||  |||||||||||||||||||||||  ||||||| X|  |||||||||||  ||||||||||||| |<br>3'- caguuacauagagaccuggagcacgugguguaagacacacccguacaacugag | SEQ ID NO: 18 | | |
| 1105-1051 | SFL CYP2C19 | ||||  |||||||||||||||||||||||  |||||| X|  |||||||||  ||||||||||||||| -<br>3'- cagcuacauagagaccuggagcacgugguguguagacacauccguacaccggg | SEQ ID NO: 19 | | |

Fig. 4b: patterns of XX

| NM pos. | match pattern | 5'- DR' . . . . . . . . . . . . . NNNNNNN . . . . . . . . UR' | match score (Fig.) 5a | 5b | 5c |
|---|---|---|---|---|---|
| 1236-1185 | IIIIXX | 5'- TGAGGTAGTTTCTGAACTTAGTATCAGTGGTCACTGCATGGGGCACACCGGT | 0.4 | 0.4 | 0.1 |
| 1235-1184 | IIIXXI | 5'- GAGGTAGTTTCTGAACTTAGTATCAGTGGTCACTGCATGGGGCACACCGGTG | 0.9 | 0.9 | 0.7 |
| 1234-1183 | IIXXII | 5'- AGGTAGTTTCTGAACTTAGTATCAGTGGTCACTGCATGGGGCACACCGGTGG | 0.4 | 0.4 | 0.1 |
| 1233-1182 | IXXIII | 5'- GGTAGTTTCTGAACTTAGTATCAGTGGTCACTGCATGGGGCACACCGGTGGG | 0.9 | 0.9 | 0.9 |
| 1232-1181 | XXIIII | 5'- GTAGTTTCTGAACTTAGTATCAGTGGTCACTGCATGGGGCACACCGGTGGGG | 0.4 | 0.9 | 0.7 |
| 1236-1181 | CYP2C8 cDNA | 5'- TGAGGTAGTTTCTGAACTTAGTATCAGTGGTCACTGCATGGGGCACACCGGTGGGG | SEQ ID NO: 8 | | |
| 1236-1181 | CYP2C8 mRNA | 3'- acuccaucaaagacuugaaucauagucaccagugacguacccgugguggccaccc | SEQ ID NO: 8 | | |
| 1166-1111 | SFL CYP2C9 | 3'- acucuauuaaagacuuaaaauuacagugu ccagugacguacccguccgaccacccc | SEQ ID NO: 9 | | |
| 1467-1412 | SFL CYP2C18 | 3'- acuccaucaaaaacuuaaauuguagugu ccagugacguaccccguccaaccacccc | SEQ ID NO: 18 | | |
| 1166-1111 | SFL CYP2C19 | 3'- acuccaucaaagacuuaaauugcagugu ccagugacguacccgu ccgaccacccc | SEQ ID NO: 19 | | |

Fig. 4c: patterns of XIX

| NM pos. | match pattern | | | match score (Fig.) 5a | 5b | 5c |
|---|---|---|---|---|---|---|
| | | 5'- DR' . . . . . . . . . . . NNNNNN . . . . . . . . . . . UR' | | | | |
| 571-522 | IIIIIX | 5'- GTTTTTCTCAACTCCTCCACAAGGCAGTGAGCTTCCTCTTGAACACGGT | | 0.1 | 0.1 | 0.1 |
| 570-521 | IIIIXI | 5'- TTTTTCTCAACTCCTCCACAAGGCAGTGAGCTTCCTCTTGAACACGGTC | | 0.1 | 0.1 | 0.1 |
| 569-520 | IIIXIX | 5'- TTTCTCAACTCCTCCACAAGGCAGTGAGCTTCCTCTTGAACACGGTCCT | | 0.9 | 0.9 | 0.4 |
| 568-519 | IIXIXI | 5'- TTCTCAACTCCTCCACAAGGCAGTGAGCTTCCTCTTGAACACGGTCCTC | | 0.9 | 0.9 | 0.7 |
| 567-518 | IXIXII | 5'- TCTCAACTCCTCCACAAGGCAGTGAGCTTCCTCTTGAACACGGTCCTCA | | 0.9 | 0.9 | 0.9 |
| 566-517 | XIXIII | 5'- CTCAACTCCTCCACAAGGCAGTGAGCTTCCTCTTGAACACGGTCCTCAA | | 0.9 | 0.7 | 0.4 |
| 565-516 | IXIIII | 5'- CTCAACTCCTCCACAAGGCAGTGAGCTTCCTCTTGAACACGGTCCTCAAT | | 0.4 | 0.4 | 0.1 |
| 564-515 | XIIIII | 5'- TCAACTCCTCCACAAGGCAGTGAGCTTCCTCTTGAACACGGTCCTCAATG | | 0.1 | 0.1 | 0.1 |
| 571-515 | CYP2C8 cDNA | 5'- GTTTTTCTCAACTCCTCCACAAGGCAGTGAGCTTCCTCTTGAACACGGTCCTCAATG | | SEQ ID NO: 8 | | |
| 571-515 | CYP2C8 mRNA | 3'- caaaaagaguugaggaguuccgucacucgaaggagaacuugugccaggaguuac | | SEQ ID NO: 8 | | |
| 501-445 | SFL CYP2C9 | 3'- caaaaagaguugaggaguuccgucXgXcccgaaggagaacuugugccaggaguuac | | SEQ ID NO: 9 | | |
| 802-746 | SFL CYP2C18 | 3'- caaaaagaguugaggaguuccgucXgXcccgaaggagaacuugugccaggagcuac | | SEQ ID NO: 18 | | |
| 501-445 | SFL CYP2C19 | 3'- caaaaagaguugaggaguuccgucXgXcccgaaggagaacuugugccaggaguuac | | SEQ ID NO: 19 | | |

Fig. 4d: patterns of XXXX and XIXIX

| NM pos. | match pattern | | | | | match score (Fig.) 5a | 5b | 5c |
|---|---|---|---|---|---|---|---|---|
| | | 5'- DR' . . . . . . . . . NNNNNN . . . . . . . . . UR' | | | | | | |
| 841-792 | IIXXXX | 5'- TTTACTTTCTCCCTAATGTAACTTCGTGTAAGAGCAACATTTTTAAGCAC | | | | 0.9 | 0.9 | 0.9 |
| 840-791 | IXXXXI | 5'- TTACTTTCTCCCTAATGTAACTTCGTGTAAGAGCAACATTTTTAAGCACT | | | | 0.9 | 0.9 | 0.9 |
| 839-790 | XXXXII | 5'- TACTTTCTCCCTAATGTAACTTCGTGTAAGAGCAACATTTTTAAGCACTT | | | | 0.9 | 0.9 | 0.9 |
| 841-790 | CYP2C8 cDNA | 5'- TTTACTTTCTCCCTAATGTAACTTCGTGTAAGAGCAACATTTTTAAGCACTT ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖ | | | | SEQ ID NO: 8 | | |
| 841-790 | CYP2C8 mRNA | 3'- aaaugaaagagggauuacauugagcacauucucguuguaaaauucgugaa | | | | SEQ ID NO: 8 | | |
| 771-720 | SFL CYP2C9 | 3'- aaaugaaaaagguuuuauauugaaaguauuuucguugcaaaauucauuaa ‖‖‖‖‖‖‖‖‖ ‖‖‖ ‖‖ ‖‖‖‖‖‖‖ ‖‖‖‖ xxxx‖‖‖ ‖‖‖ ‖‖‖‖‖‖‖‖‖‖ ‖‖‖ | | | | SEQ ID NO: 9 | | |
| 707-656 | IXIXIX | 5'- GTTTTCATTGAATCTTTTCATCAGGGTGAGAAAATTCTGATCTTTATAAT | | | | 0.9 | 0.9 | 0.9 |
| 706-655 | XIXIXI | 5'- TTTTCATTGAATCTTTTCATCAGGGTGAGAAAATTCTGATCTTTATAATC | | | | 0.9 | 0.9 | 0.9 |
| 707-655 | CYP2C8 cDNA | 5'- GTTTTCATTGAATCTTTTCATCAGGGTGAGAAAATTCTGATCTTTATAATC ‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖‖ | | | | SEQ ID NO: 8 | | |
| 707-655 | CYP2C8 mRNA | 3'- caaaaguaacuuagaaaguagucccacucuuuuaagacuagaaauauuag | | | | SEQ ID NO: 8 | | |
| 938-888 | SFL CYP2C18 | 3'- caaaaguaacuuaaaagguaaguucaauucuuuggagacuagaaauauuag ‖‖‖‖‖‖‖‖‖‖‖‖ ‖‖ ‖‖‖ ‖ ‖‖‖ x‖x‖x‖ ‖‖‖ ‖‖‖‖‖‖‖‖‖‖‖‖‖‖‖‖‖‖‖ | | | | SEQ ID NO: 18 | | |

Fig. 4e: patterns of XXIIXX

|  |  |  | match score (Fig.) | | |
|---|---|---|---|---|---|
| NM pos. | match pattern | 5'-DR'. . . . . . . . . .NNNNNN. . . . . . . . . . . .UR' | 5a | 5b | 5c |
| 513-464 | IIIIIX | 5'- TCCTCTTCCCATCCCAAAATTCCGCAAGTTGTGAGGGAGAAACGCCGG | 0.1 | 0.1 | 0.1 |
| 512-463 | IIIIXX | 5'- CCTCTTCCCATCCCAAAATTCCGCAAGTTGTGAGGGAGAAACGCCGGA | 0.4 | 0.4 | 0.1 |
| 511-462 | IIIXXI | 5'- CTCTTCCCATCCCAAAATTCCGCAAGTTGTGAGGGAGAAACGCCGGAT | 0.9 | 0.9 | 0.7 |
| 510-461 | IIXXII | 5'- TCTTCCCATCCCAAAATTCCGCAAGTTGTGAGGGAGAAACGCCGGATC | 0.4 | 0.4 | 0.1 |
| 509-460 | IXXIIX | 5'- CTTCCCATCCCAAAATTCCGCAAGTTGTGAGGGAGAAACGCCGGATCT | 0.9 | 0.9 | 0.4 |
| 508-459 | XXIIXX | 5'- TTCCCATCCCAAAATTCCGCAAGTTGTGAGGGAGAAACGCCGGATCTC | 0.7 | 0.4 | 0.4 |
| 507-458 | XIIXXI | 5'- TCCCCATCCCAAAATTCCGCAAGTTGTGAGGGAGAAACGCCGGATCTCC | 0.9 | 0.9 | 0.9 |
| 506-457 | IIXXII | 5'- CCCCATCCCAAAATTCCGCAAGTTGTGAGGGAGAAACGCCGGATCTCCT | 0.4 | 0.4 | 0.1 |
| 505-456 | IXXIII | 5'- CCCATCCCAAAATTCCGCAAGTTGTGAGGGAGAAACGCCGGATCTCCTT | 0.9 | 0.9 | 0.9 |
| 504-455 | XXIIII | 5'- CCATCCCAAAATTCCGCAAGTTGTGAGGGAGAAACGCCGGATCTCCTTC | 0.4 | 0.9 | 0.7 |
| 503-454 | XIIIII | 5'- CATCCCAAAATTCCGCAAGTTGTGAGGGAGAAACGCCGGATCTCCTTCC | 0.1 | 0.1 | 0.1 |
| 513-454 | *CYP2C8* cDNA | 5'- TCCTCTTCCCATCCCAAAATTCCGCAAGTTGTGAGGGAGAAACGCCGGATCTCCTTCC | SEQ ID NO: 8 | | |
| 513-454 | *CYP2C8* mRNA | 3'- aggagaaggguaggguuuuaaggcguuccaacacuccccucuuugcggccuagaggaagg | SEQ ID NO: 8 | | |
| 443-384 | SFL *CYP2C19* | 3'- aggagaagggguaggguuuuaaggcgucgcaguacuccccucuuugcggccuagaggaagg | SEQ ID NO: 19 | | |

Fig. 5: Combinations of mutated attenuators upstream detectors:

| downstream detectors: | | wildtype p-GGA- | 2b_U p-GGt- | 1b_U p-GcA- | 0b_U p-cGA- | 5b_U p-Gct- | 3b_U p-cGt- | 6b_U p-ccA- | 4b_U p-cct- |
|---|---|---|---|---|---|---|---|---|---|
| wildtype | -CCA | 100.000% | 74.118% | 28.224% | 1.232% | 12.792% | 0.207% | 0.056% | 0.028% |
| 2b_D | -gCA | 61.590% | 33.058% | 9.710% | 0.363% | 3.137% | 0.023% | 0.000% | 0.000% |
| 1b_D | -CgA | 2.183% | 0.778% | 0.215% | 0.011% | 0.047% | 0.000% | 0.050% | 0.000% |
| 0b_D | -CCt | 0.844% | 0.229% | 0.082% | 7.299% | 0.008% | 0.803% | 0.075% | 0.007% |
| 5b_D | -ggA | 0.081% | 0.509% | 0.061% | 0.000% | 1.169% | 0.058% | 0.017% | 0.041% |
| 3b_D | -gCt | 0.221% | 0.139% | 0.013% | 1.423% | 0.000% | 0.201% | 0.005% | 0.005% |
| 6b_D | -Cgt | 0.009% | 0.000% | 0.000% | 0.010% | 0.000% | 0.000% | 0.000% | 0.000% |
| 4b_D | -ggt | 0.000% | 0.032% | 0.000% | 0.000% | 0.000% | 0.020% | 0.006% | 0.000% |

*Fig. 5a: Match Scores (MS) for matches (I) or mismatches (X) with SFL*

ULSB matches with FLS:

|  |  | p-I- |  |  |  | p-X- |  |  |  |
|---|---|---|---|---|---|---|---|---|---|
|  |  |  | p-II- |  | p-IX- | p-XI- |  |  | p-XX- |
|  |  | p-III- | p-IIX- | p-IXI- | p-XII- | p-IXX- | p-XIX- | p-XXI- | p-XXX- |
| -I- | -III- | 0.1 | 0.1 | 0.1 | 0.4 | 0.4 | 0.9 | 0.9 | 0.9 |
|  | -IIX- | 0.1 | 0.1 | 0.4 | 0.9 | 0.7 | 0.9 | 0.9 | 0.9 |
|  | -IXI- | 0.4 | 0.7 | 0.9 | 0.9 | 0.9 | 0.9 | 0.9 | 0.9 |
| -X- | -XII- | 0.4 | 0.7 | 0.9 | 0.4 | 0.9 | 0.7 | 0.9 | 0.9 |
|  | -IXX- | 0.4 | 0.4 | 0.7 | 0.9 | 0.7 | 0.9 | 0.9 | 0.9 |
|  | -XIX- | 0.9 | 0.9 | 0.9 | 0.9 | 0.9 | 0.9 | 0.9 | 0.9 |
| -XX- | -XXI- | 0.9 | 0.9 | 0.9 | 0.9 | 0.9 | 0.9 | 0.9 | 0.9 |
|  | -XXX- | 0.9 | 0.9 | 0.9 | 0.9 | 0.9 | 0.9 | 0.9 | 0.9 |

DLSB matches with FLS

*Fig. 5b: First alternate set of Match Scores*

ULSB matches with FLS:

| | | p-I- | | | p-X- | | | p-XX- | |
|---|---|---|---|---|---|---|---|---|---|
| DLSB matches with FLS: | p-I- | p-II- | p-IX- | p-XI- | p-XII- | p-XIX- | p-XXI- | p-XXX- |
| -I- | -III- | 0.1 | 0.1 | 0.1 | 0.4 | 0.4 | 0.4 | 0.9 | 0.9 |
| | -XII- | 0.1 | 0.1 | 0.4 | 0.9 | 0.4 | 0.9 | 0.9 | 0.9 |
| | -XI- | 0.4 | 0.7 | 0.9 | 0.9 | 0.4 | 0.9 | 0.9 | 0.9 |
| -X- | -IIX- | 0.4 | 0.7 | 0.9 | 0.4 | 0.9 | 0.4 | 0.9 | 0.9 |
| | -XXI- | 0.9 | 0.4 | 0.9 | 0.9 | 0.9 | 0.9 | 0.9 | 0.9 |
| | -XIX- | 0.7 | 0.9 | 0.9 | 0.4 | 0.4 | 0.9 | 0.9 | 0.9 |
| -XX- | -IXX- | 0.9 | 0.9 | 0.9 | 0.9 | 0.9 | 0.9 | 0.9 | 0.9 |
| | -XXX- | 0.9 | 0.9 | 0.9 | 0.9 | 0.9 | 0.9 | 0.9 | 0.9 |

Fig. 5c: second alternate set (stringent) for Match Scores

ULSB matches with FLS:

| DLSB matches with FLS: | | p-I- | | | | p-X- | | | p-XX- | |
|---|---|---|---|---|---|---|---|---|---|---|
| | | p-II- | p-XII- | p-IX- | p-XI- | p-XII- | p-IXX- | p-XIX- | p-XXI- | p-XXX- |
| -I | -III- | 0.1 | 0.1 | 0.1 | 0.4 | 0.1 | 0.1 | 0.4 | 0.7 | 0.9 |
| -II | -XII- | 0.1 | 0.1 | 0.1 | 0.4 | 0.4 | 0.1 | 0.9 | 0.9 | 0.9 |
| | -IXI- | 0.1 | 0.4 | 0.4 | 0.9 | 0.9 | 0.9 | 0.9 | 0.7 | 0.9 |
| -IX | -XII- | 0.4 | 0.4 | 0.7 | 0.1 | 0.9 | 0.4 | 0.4 | 0.7 | 0.9 |
| -XI | -XXI- | 0.7 | 0.4 | 0.7 | 0.9 | 0.4 | 0.9 | 0.7 | 0.9 | 0.9 |
| | -XIX- | 0.4 | 0.7 | 0.9 | 0.4 | 0.9 | 0.4 | 0.4 | 0.9 | 0.9 |
| -XX | -XXI- | 0.9 | 0.9 | 0.9 | 0.9 | 0.9 | 0.9 | 0.9 | 0.9 | 0.9 |
| | -XXX- | 0.9 | 0.9 | 0.9 | 0.9 | 0.9 | 0.9 | 0.9 | 0.9 | 0.9 |

Fig. 6: comparison with exon-junction probes

| NM pos. | | | 5' DR' . . . . . . . . . . . . NNNNNN . . . . . . . . . . UR' | match score (Fig.) 5a | 5b | 5c | GC content per probe DR' % | UR' % | score |
|---|---|---|---|---|---|---|---|---|---|
| 288-239 | a\|b | junction | 5'- ACACAGGACCATAGACTTTTGAGAAAATTGGTGAAAGATTTGCAGATGTCC | 0.1 | 0.1 | 0.1 | 40% | 40% | 1.0 |
| 519-470 | SFL | CYP2C18 | 3'- uguguccgguaucugaaaaccuuuaaccaauuccuaaacgaguacagg | | | | | | |
| 451-402 | b\|c | junction | 5'- CTCTTTCCATTGCTGGAAATGATTCCAAGTCCTTTAGTAATTCTTTGAGA | 0.1 | 0.1 | 0.1 | 40% | 32% | 0.4 |
| 682-633 | SFL | CYP2C18 | 3'- gagaaagguaacgacuuuuccuaagguucaggaaacaauugaaaagucg | | | | | | |
| 601-552 | c\|d | junction | 5'- ATGAAAGTGGATCACAGGGTGAAGCCTTGGTTTTTCTCAACTCCTCCAC | 0.1 | 0.1 | 0.1 | 40% | 44% | 1.0 |
| 531-482 | SFL | CYP2C19 | 3'- uacuuucacccuagugucccacuucggaaccaaaaagaguugaggaggug | | | | | | |
| 762-713 | d\|e | junction | 5'- TGAGTAGAGGGAAATTATTGCAGACCTGGATCCATGGGGAGTTCAGAATC | 0.1 | 0.1 | 0.1 | 40% | 48% | 1.0 |
| 993-944 | SFL | CYP2C18 | 3'- acucucguccuuuaauaacgucuggacuaggu accucucgagucuuag | | | | | | |
| 939-890 | e\|f | junction | 5'- ATTCTGACTTTTGGTTGTCCTTTTCCTGCTCCATTTTGATCAGGAAGCAA | 0.1 | 0.1 | 0.1 | 36% | 40% | 0.7 |
| 869-820 | SFL | CYP2C19 | 3'- uaagucugacaaccaaaacgaaaaggaagaaguaaaacuagucccuucguu | | | | | | |

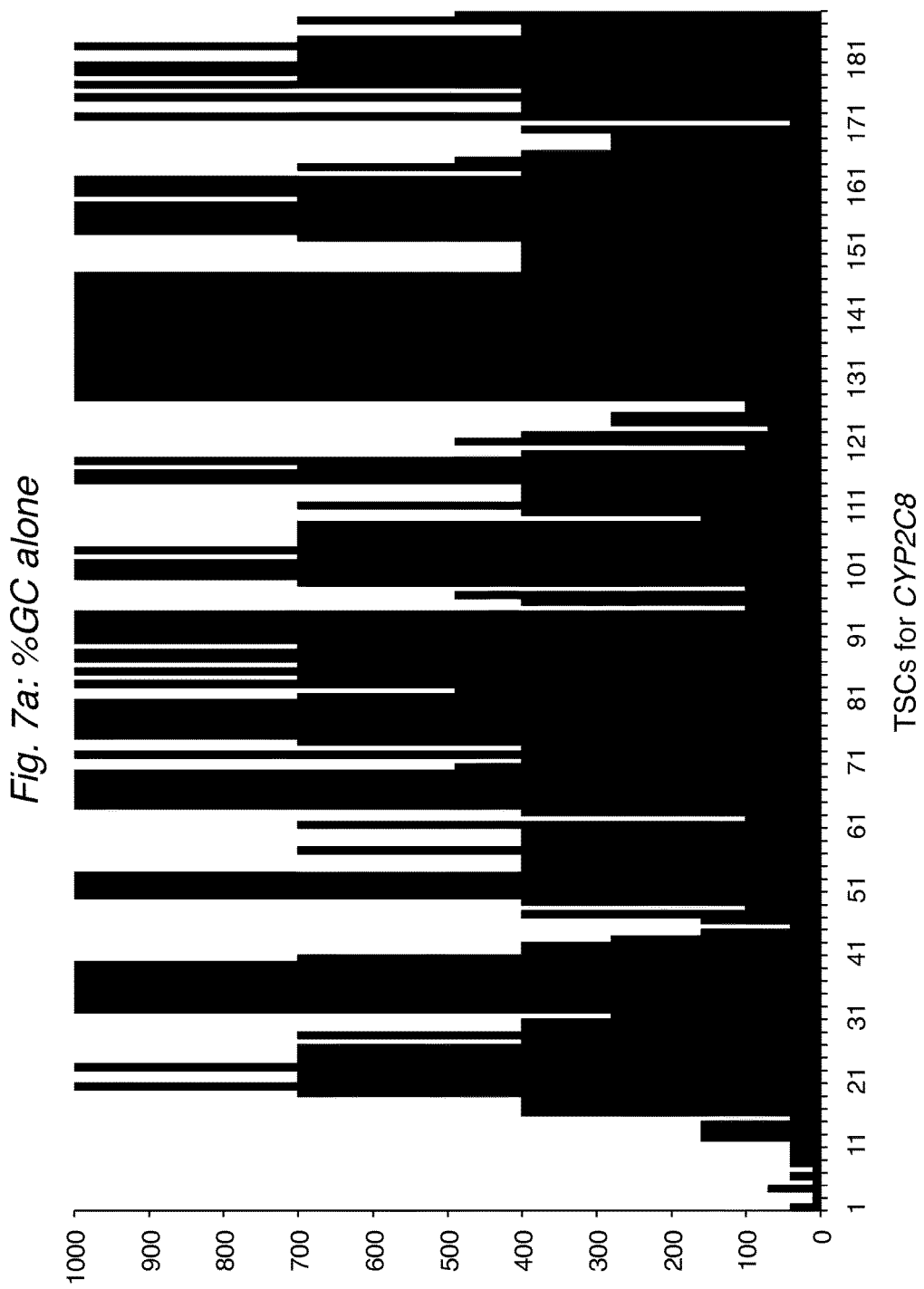

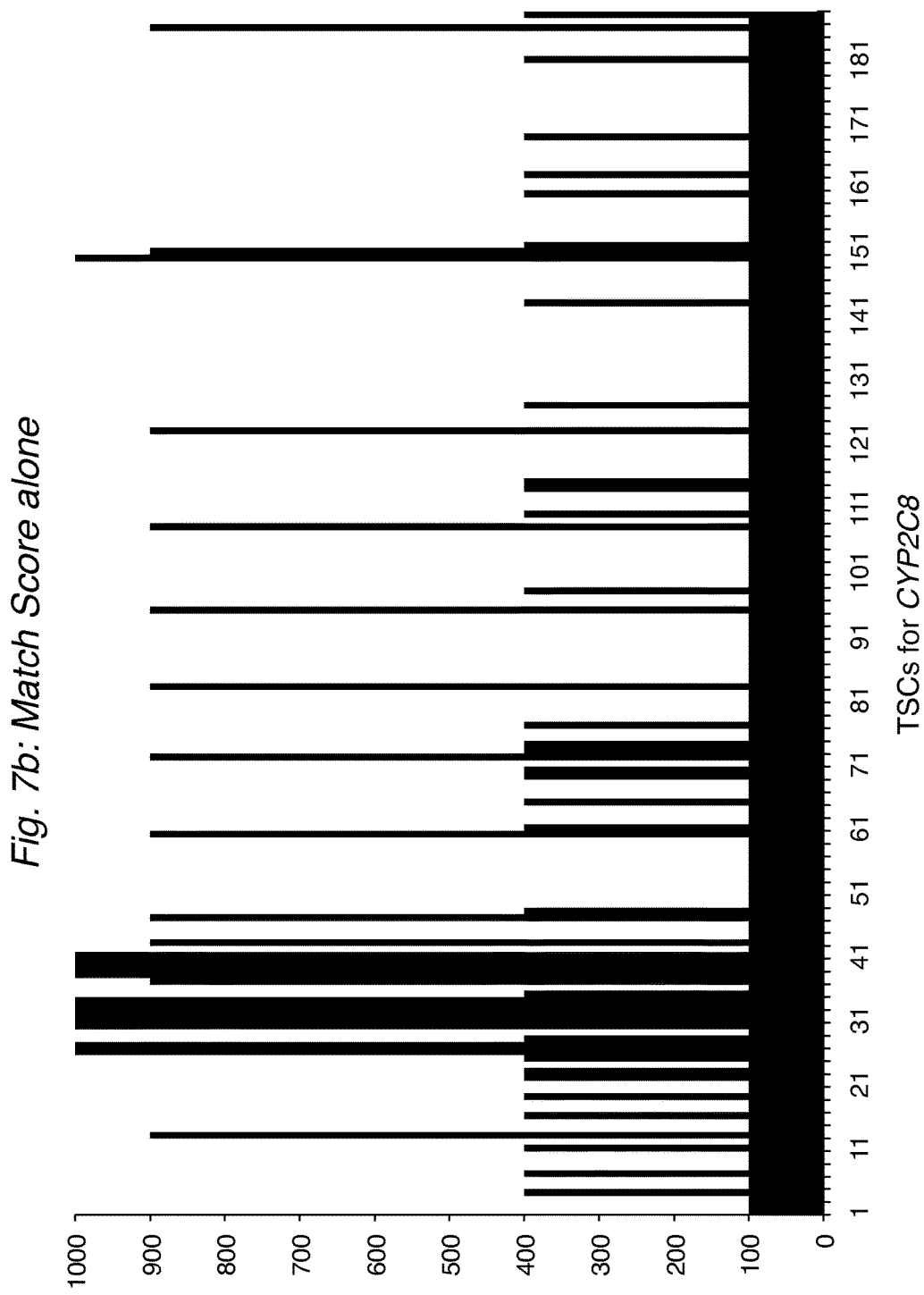

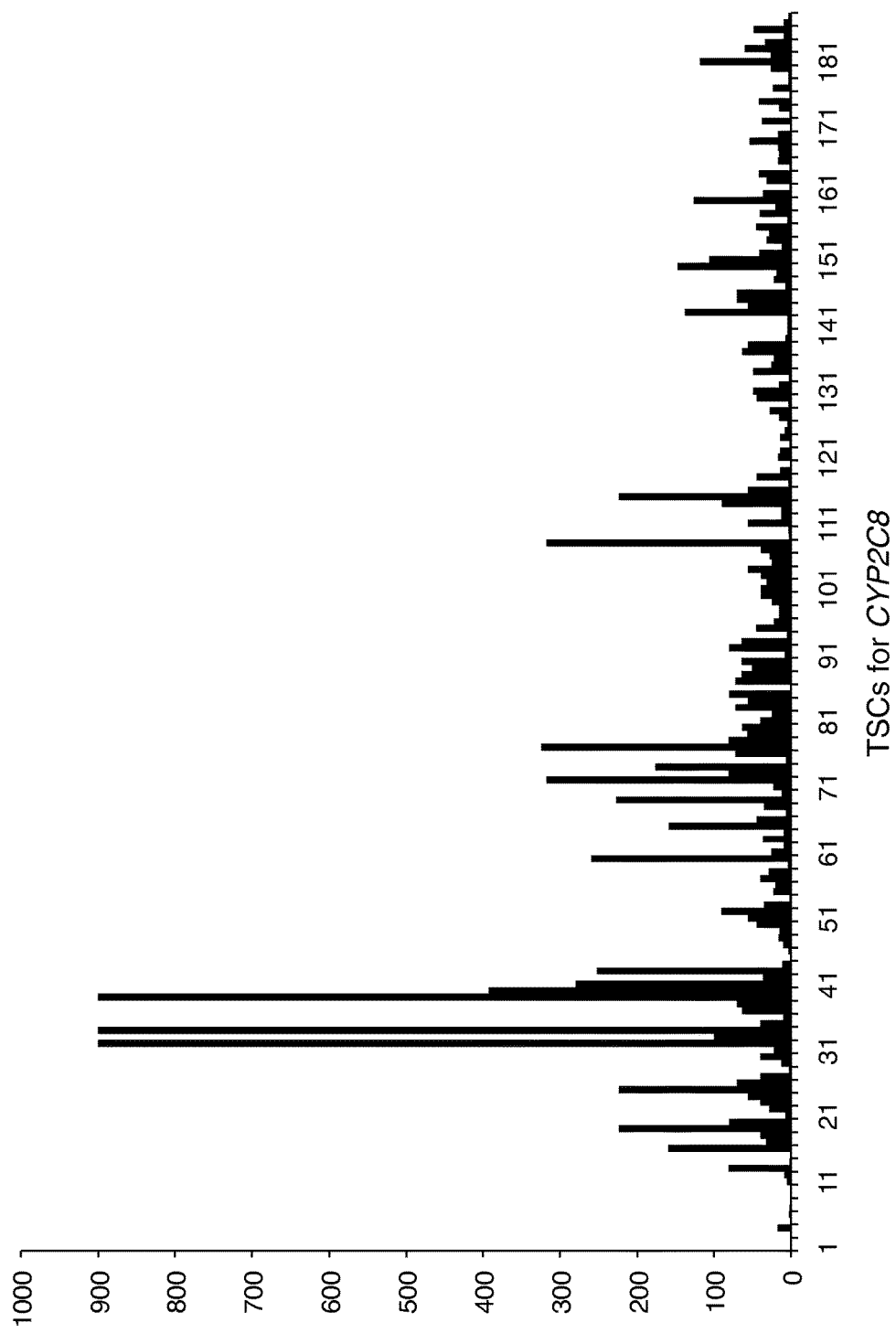

US 9,938,566 B2

SEQUENCE LISTING

<160> NUMBER OF SEQ ID NOS: 19

<210> SEQ ID NO 1
<211> LENGTH: 50
<212> TYPE: RNA
<213> ORGANISM: Homo sapiens

<400> SEQUENCE: 1
cgaccacuuu gucaagcuca uuccuggua ugacaacgaa uuuggcuaca          50

<210> SEQ ID NO 2
<211> LENGTH: 25
<212> TYPE: RNA
<213> ORGANISM: Homo sapiens

<400> SEQUENCE: 2
ugguaugaca acgaauuugg cuaca                                   25

<210> SEQ ID NO 3
<211> LENGTH: 25
<212> TYPE: DNA
<213> ORGANISM: Homo sapiens

<400> SEQUENCE: 3
tgtagccaaa ttcgttgtca tacca                                   25

<210> SEQ ID NO 4
<211> LENGTH: 25
<212> TYPE: RNA
<213> ORGANISM: Homo sapiens

<400> SEQUENCE: 4
cgaccacuuu gucaagcuca uuucc                                   25

<210> SEQ ID NO 5
<211> LENGTH: 25
<212> TYPE: DNA
<213> ORGANISM: Homo sapiens

<400> SEQUENCE: 5
ggaaatgagc ttgacaaagt ggtcg                                   25

<210> SEQ ID NO 6
<211> LENGTH: 6
<212> TYPE: DNA
<213> ORGANISM: Homo sapiens

<400> SEQUENCE: 6 ccagga                                                         6

<210> SEQ ID NO 7
<211> LENGTH: 6
<212> TYPE: DNA
<213> ORGANISM: Artificial Sequence
<220> FEATURE:
<223> OTHER INFORMATION: Synthetic junction sequence formed by ligation
      of mutated oligos

<400> SEQUENCE: 7 gcaggt                                                         6

<210> SEQ ID NO 8
<211> LENGTH: 1924
<212> TYPE: DNA

<213> ORGANISM: Homo sapiens

<400> SEQUENCE: 8

| | |
|---|---|
| acatgtcaaa gagacacaca ctaaattagc agggagtgtt ataaaaactt tggagtgcaa | 60 |
| gctcacagct gtcttaataa gaagagaagg cttcaatgga accttttgtg gtcctggtgc | 120 |
| tgtgtctctc ttttatgctt ctcttttcac tctggagaca gagctgtagg agaaggaagc | 180 |
| tccctcctgg ccccactcct cttcctatta ttggaaatat gctacagata gatgttaagg | 240 |
| acatctgcaa atctttcacc aatttctcaa aagtctatgg tcctgtgttc accgtgtatt | 300 |
| ttggcatgaa tcccatagtg gtgtttcatg gatatgaggc agtgaaggaa gccctgattg | 360 |
| ataatggaga ggagttttct ggaagaggca attccccaat atctcaaaga attactaaag | 420 |
| gacttggaat catttccagc aatggaaaga gatggaagga gatccggcgt ttctccctca | 480 |
| caaccttgcg gaattttggg atggggaaga ggagcattga ggaccgtgtt caagaggaag | 540 |
| ctcactgcct tgtggaggag ttgagaaaaa ccaaggcttc accctgtgat cccactttca | 600 |
| tcctgggctg tgctccctgc aatgtgatct gctccgttgt tttccagaaa cgatttgatt | 660 |
| ataaagatca gaattttctc accctgatga aagattcaa tgaaaacttc aggattctga | 720 |
| actcccatg gatccaggtc tgcaataatt ccctctact cattgattgt ttcccaggaa | 780 |
| ctcacaacaa agtgcttaaa aatgttgctc ttacacgaag ttacattagg gagaaagtaa | 840 |
| aagaacacca agcatcactg gatgttaaca atcctcggga ctttatcgat tgcttcctga | 900 |
| tcaaaatgga gcaggaaaag gacaaccaaa agtcagaatt caatattgaa aacttggttg | 960 |
| gcactgtagc tgatctcttt gttgctggaa cagagacaac aagcaccact ctgagatatg | 1020 |
| gactcctgct cctgctgaag cacccagagg tcacagctaa agtccaggaa gagattgatc | 1080 |
| atgtaattgg cagacacagg agccctgca tgcaggatag gagccacatg ccttacactg | 1140 |
| atgctgtagt gcacgagatc cagagataca gtgaccttgt ccccaccggt gtgccccatg | 1200 |
| cagtgaccac tgtatactaag ttcagaaact acctcatccc caagggcaca accataatgg | 1260 |
| cattactgac ttccgtgcta catgatgaca agaatttcc taatccaaat atctttgacc | 1320 |
| ctggccactt tctagataag aatggcaact ttaagaaaag tgactacttc atgcctttct | 1380 |
| cagcaggaaa acgaatttgt gcaggagaag gacttgcccg catggagcta ttttatttc | 1440 |
| taaccacaat tttacagaac tttaacctga atctgttga tgatttaaag aacctcaata | 1500 |
| ctactgcagt taccaaaggg attgtttctc tgccaccctc ataccagatc tgcttcatcc | 1560 |
| ctgtctgaag aatgctagcc catctggctg ccgatctgct atcacctgca actctttttt | 1620 |
| tatcaaggac attcccacta ttatgtcttc tctgacctct catcaaatct tcccattcac | 1680 |
| tcaatatccc ataagcatcc aaactccatt aaggagagtt gttcaggtca ctgcacaaat | 1740 |
| atatctgcaa ttattcatac tctgtaacac ttgtattaat tgctgcatat gctaatactt | 1800 |
| ttctaatgct gactttttaa tatgttatca ctgtaaaaca cagaaaagtg attaatgaat | 1860 |
| gataaattag atccatttct tttgtgaatg tgctaaataa aaagtgttat taattgctgg | 1920 |
| ttca | 1924 |

<210> SEQ ID NO 9
<211> LENGTH: 1876
<212> TYPE: DNA
<213> ORGANISM: Homo sapiens

<400> SEQUENCE: 9

| | |
|---|---|
| gtcttaacaa gaagagaagg cttcaatgga ttctcttgtg gtccttgtgc tctgtctctc | 60 |

```
atgtttgctt ctcctttcac tctggagaca gagctctggg agaggaaaac tccctcctgg      120
ccccactcct ctcccagtga ttggaaatat cctacagata ggtattaagg acatcagcaa      180
atccttaacc aatctctcaa aggtctatgg ccctgtgttc actctgtatt ttggcctgaa      240
acccatagtg gtgctgcatg gatatgaagc agtgaaggaa gccctgattg atcttggaga      300
ggagttttct ggaagaggca ttttcccact ggctgaaaga gctaacagag gatttggaat      360
tgttttcagc aatggaaaga atggaaggga gatccggcgt ttctccctca tgacgctgcg      420
gaatttgggg atggggaaga ggagcattga ggaccgtgtt caagaggaag cccgctgcct      480
tgtggaggag ttgagaaaaa ccaaggcctc accctgtgat cccactttca tcctgggctg      540
tgctccctgc aatgtgatct gctccattat tttccataaa cgttttgatt ataaagatca      600
gcaatttctt aacttaatgg aaaagttgaa tgaaaacatc aagattttga gcagcccctg      660
gatccagatc tgcaataatt tttctcctat cattgattac ttcccgggaa ctcacaacaa      720
attacttaaa aacgttgctt ttatgaaaag ttatattttg gaaaaagtaa aagaacacca      780
agaatcaatg gacatgaaca accctcagga ctttattgat tgcttcctga tgaaaatgga      840
gaaggaaaag cacaaccaac catctgaatt tactattgaa agcttggaaa acactgcagt      900
tgacttgttt ggagctggga cagagacgac aagcacaacc ctgagatatg ctctccttct      960
cctgctgaag cacccagagg tcacagctaa agtccaggaa gagattgaac gtgtgattgg     1020
cagaaaccgg agccctgcat gcaagacagg agccacatg cctacacag atgctgtggt     1080 gcacgaggtc cagagataca ttgaccttct ccccaccagc ctgccccatg cagtgacctg     1140
tgacattaaa ttcagaaact atctcattcc caagggcaca accatattaa tttccctgac     1200
ttctgtgcta catgacaaca aagaatttcc caacccagag atgtttgacc ctcatcactt     1260
tctggatgaa ggtggcaatt ttaagaaaag taaatacttc atgcctttct cagcaggaaa     1320
acggatttgt gtgggagaag ccctggccgg catgggagctg tttttattcc tgacctccat     1380
tttacagaac tttaacctga atctctggt tgacccaaag aaccttgaca ccactccagt     1440
tgtcaatgga tttgcctctg tgccgcccctt ctaccagctg tgcttcattc ctgtctgaag     1500
aagagcagat ggcctggctg ctgctgtgca gtccctgcag ctctctttcc tctggggcat     1560
tatccatctt tcactatctg taatgccttt tctcacctgt catctcacat tttcccttcc     1620
ctgaagatct agtgaacatt cgacctccat tacggagagt ttcctatgtt tcactgtgca     1680
aatatatctg ctattctcca tactctgtaa cagttgcatt gactgtcaca taatgctcat     1740
acttatctaa tgttgagtta ttaatatgtt attattaaat agagaaatat gatttgtgta     1800
ttataattca aaggcatttc ttttctgcat gttctaaata aaaagcatta ttatttgctg     1860
aaaaaaaaaa aaaaaa                                                     1876
```

<210> SEQ ID NO 10
<211> LENGTH: 22
<212> TYPE: DNA
<213> ORGANISM: Artificial Sequence
<220> FEATURE:
<223> OTHER INFORMATION: Synthetic P1 downstream amplification sequence
      or primer

<400> SEQUENCE: 10
caagcagaag acggcatacg ag                                               22

<210> SEQ ID NO 11
<211> LENGTH: 23

```
<212> TYPE: DNA
<213> ORGANISM: Artificial Sequence
<220> FEATURE:
<223> OTHER INFORMATION: Synthetic P2' upstream amplification sequence

<400> SEQUENCE: 11
atctcggtgg tcgccgtatc att                                              23

<210> SEQ ID NO 12
<211> LENGTH: 23
<212> TYPE: DNA
<213> ORGANISM: Artificial Sequence
<220> FEATURE:
<223> OTHER INFORMATION: Synthetic P2 amplification primer

<400> SEQUENCE: 12
aatgatacgg cgaccaccga gat                                              23

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 13
tttttttttt tttttttttt ttttt                                            25

<210> SEQ ID NO 14
<211> LENGTH: 6
<212> TYPE: DNA
<213> ORGANISM: Artificial Sequence
<220> FEATURE:
<223> OTHER INFORMATION: Synthetic junction sequence formed by ligation
      of mutated oligos

<400> SEQUENCE: 14 ggacgt                                                                  6

<210> SEQ ID NO 15
<211> LENGTH: 56
<212> TYPE: RNA
<213> ORGANISM: Homo sapiens

<400> SEQUENCE: 15
cucgcaguga aggaagcccu gauugaucuu ggagaggagu uuucuggaag aguugg          56

<210> SEQ ID NO 16
<211> LENGTH: 56
<212> TYPE: RNA
<213> ORGANISM: Homo sapiens

<400> SEQUENCE: 16
cucgcaguga aggaagcccu gauugauaau ggagaggagu uuucuggaag aguugg          56

<210> SEQ ID NO 17
<211> LENGTH: 56
<212> TYPE: RNA
<213> ORGANISM: Homo sapiens

<400> SEQUENCE: 17
cucgcaguga aggaagcccu gauugaucau ggagaggagu uuucuggaag aguugg          56

<210> SEQ ID NO 18
<211> LENGTH: 2562
```

```
<212> TYPE: DNA
<213> ORGANISM: Homo sapiens

<400> SEQUENCE: 18
```

| | | | | | |
|---|---|---|---|---|---|
| gagatcttgc | cattgcactc | cagcctgggc | aacaagagcg | aaactccatc | tcaaggaaaa        60 |
| acaacaacaa | caacaacaaa | atcctgggct | ctgcttcaga | ctagttaaac | cagaatctcc       120 |
| agggtggggc | accggaaaga | acaagaaaaa | agaacacctt | attttttatct | tcttcagtga       180 |
| gccaatgttc | attcaaaaga | gagattaaag | tgcttttttgc | tgactagtca | cagtcagagt       240 |
| cagaatcaca | ggtggattag | tagggagtgt | tataaaagcc | ttgaagtgaa | agcccgcagt       300 |
| tgtcttacta | agaagagaag | ccttcaatgg | atccagctgt | ggctctggtg | ctctgtctct       360 |
| cctgtttgtt | tctcctttca | ctctggaggc | agagctctgg | aagagggagg | ctcccgtctg       420 |
| gccccactcc | tctcccgatt | attggaaata | tcctgcagtt | agatgttaag | gacatgagca       480 |
| aatccttaac | caatttctca | aaagtctatg | gccctgtgtt | cactgtgtat | tttggcctga       540 |
| agcccattgt | ggtgttgcat | ggatatgaag | cagtgaagga | ggccctgatt | gatcatggag       600 |
| aggagttttc | tggaagagga | agttttccag | tggctgaaaa | agttaacaaa | ggacttggaa       660 |
| tcctttttcag | caatggaaag | agatggaagg | agatccggcg | tttctgcctc | atgactctgc       720 |
| ggaattttgg | gatggggaag | aggagcatcg | aggaccgtgt | tcaagaggaa | gcccgctgcc       780 |
| ttgtggagga | gttgagaaaa | accaatgcct | caccctgtga | tcccactttc | atcctgggct       840 |
| gtgctccctg | caatgtgatc | tgctctgtta | ttttccatga | tcgatttgat | tataaagatc       900 |
| agaggttttct | taacttgatg | gaaaaattca | atgaaaacct | caggattctg | agctctccat       960 |
| ggatccaggt | ctgcaataat | ttccctgctc | tcatcgatta | tctcccagga | agtcataata      1020 |
| aaatagctga | aaattttgct | tacattaaaa | gttatgtatt | ggagagaata | aaagaacatc      1080 |
| aagaatccct | ggacatgaac | agtgctcggg | actttattga | ttgtttcctg | atcaaaatgg      1140 |
| aacaggaaaa | gcacaatcaa | cagtctgaat | ttactgttga | aagcttgata | gccactgtaa      1200 |
| ctgatatgtt | tggggctgga | acagagacaa | cgagcaccac | tctgagatat | ggactcctgc      1260 |
| tcctgctgaa | gtacccagag | gtcacagcta | aagtccagga | agagattgaa | tgtgtagttg      1320 |
| gcagaaaccg | gagcccctgt | atgcaggaca | ggagtcacat | gccctacaca | gatgctgtgg      1380 |
| tgcacgagat | ccagagatac | attgacctcc | tccccaccaa | cctgcccat | gcagtgacct      1440 |
| gtgatgttaa | attcaaaaac | tacctcatcc | ccaagggcac | gaccataata | acatccctga      1500 |
| cttctgtgct | gcacaatgac | aaagaattcc | ccaacccaga | gatgtttgac | cctggccact      1560 |
| ttctggataa | gagtggcaac | tttaagaaaa | gtgactactt | catgccttttc | tcagcaggaa      1620 |
| aacggatgtg | tatgggagag | ggcctggccc | gcatggagct | gttttttattc | ctgaccacca      1680 |
| ttttgcagaa | ctttaacctg | aaatctcagg | ttgacccaaa | ggatattgac | atcacccca      1740 |
| ttgccaatgc | atttggtcgt | gtgccaccct | tgtaccagct | ctgcttcatt | cctgtctgaa      1800 |
| gaagggcaga | tagtttggct | gctcctgtgc | tgtcacctgc | aattctccct | tatcagggcc      1860 |
| attggcctct | cccttctctc | tgtgagggat | attttctctg | acttgtcaat | ccacatcttc      1920 |
| ccattccctc | aagatccaat | gaacatccaa | cctccattaa | agagagtttc | ttgggtcact      1980 |
| tcctaaatat | atctgctatt | ctccatactc | tgtatcactt | gtattgacca | ccacatatgc      2040 |
| taatacctat | ctactgctga | gttgtcagta | tgttatcact | agaaaacaaa | gaaaaatgat      2100 |
| taataaatga | caattcagag | ccatttattc | tctgcatgct | ctagataaaa | atgattatta      2160 |
| tttactgggt | cagttcttag | atttcttttct | tttgagtaaa | atgaaagtaa | gaaatgaaag      2220 |

| aaaatagaat gtgaagaggc tgtgctggcc ctcatagtgt taagcacaaa aagggagaaa | 2280 |
| ggtaagaggg taggaaagct gttttagcta aatgccacct agagttattg gaggtctgaa | 2340 |
| tttggaaaaa aaactatgt ccaggagcag ctgtaacctg tagggaaata ctggaacaat | 2400 |
| catccataag agggatgaac attaagtgtt tgaattcatg ctctgctttt gtgttactgt | 2460 |
| aaacacaaga tcaagatttg gataatcttt ttcctttgtg tttccaactt agatcatgtc | 2520 |
| taaatatatg ctttcatatg gctaaaaaaa aaaaaaaaaa aa | 2562 |

<210> SEQ ID NO 19
<211> LENGTH: 1799
<212> TYPE: DNA
<213> ORGANISM: Homo sapiens

<400> SEQUENCE: 19

| gtcttaacaa gaggagaagg cttcaatgga tccttttgtg gtccttgtgc tctgtctctc | 60 |
| atgtttgctt ctcctttcaa tctggagaca gagctctggg agaggaaaac tccctcctgg | 120 |
| ccccactcct ctcccagtga ttggaaatat cctacagata gatattaagg atgtcagcaa | 180 |
| atccttaacc aatctctcaa aaatctatgg ccctgtgttc actctgtatt ttggcctgga | 240 |
| acgcatggtg gtgctgcatg gatatgaagt ggtgaaggaa gccctgattg atcttggaga | 300 |
| ggagttttct ggaagaggcc atttcccact ggctgaaaga gctaacagag gatttggaat | 360 |
| cgttttcagc aatggaaaga gatggaagga gatccggcgt ttctccctca tgacgctgcg | 420 |
| gaattttggg atggggaaga ggagcattga ggaccgtgtt caagaggaag cccgctgcct | 480 |
| tgtggaggag ttgagaaaaa ccaaggcttc accctgtgat cccactttca tcctgggctg | 540 |
| tgctccctgc aatgtgatct gctccattat tttccagaaa cgtttcgatt ataaagatca | 600 |
| gcaatttctt aacttgatgg aaaaattgaa tgaaaacatc aggattgtaa gcaccccctg | 660 |
| gatccagata tgcaataatt ttcccactat cattgattat ttcccgggaa cccataacaa | 720 |
| attacttaaa aaccttgctt ttatggaaag tgatattttg gagaaagtaa agaacacca | 780 |
| agaatcgatg gacatcaaca ccctcgggga ctttattgat tgcttcctga tcaaaatgga | 840 |
| gaaggaaaag caaaaccaac agtctgaatt cactattgaa aacttggtaa tcactgcagc | 900 |
| tgacttactt ggagctggga cagagacaac aagcacaacc ctgagatatg ctctccttct | 960 |
| cctgctgaag cacccagagg tcacagctaa agtccaggaa gagattgaac gtgtcattgg | 1020 |
| cagaaaccgg agccctgca tgcaggacag gggccacatg ccctacacag atgctgtggt | 1080 |
| gcacgaggtc cagagataca tcgacctcat ccccaccagc ctgccccatg cagtgacctg | 1140 |
| tgacgttaaa ttcagaaact acctcattcc caagggcaca accatattaa cttccctcac | 1200 |
| ttctgtgcta catgacaaca aagaatttcc caacccagag atgtttgacc ctcgtcactt | 1260 |
| tctggatgaa ggtggaaatt ttaagaaaag taactacttc atgcctttct cagcaggaaa | 1320 |
| acggatttgt gtgggagagg gcctggcccg catggagctg tttttattcc tgaccttcat | 1380 |
| tttacagaac tttaacctga atctctgat tgacccaaag gaccttgaca caactcctgt | 1440 |
| tgtcaatgga tttgcttctg tcccgccctt ctatcagctg tgcttcattc ctgtctgaag | 1500 |
| aagcacagat ggtctggctg ctcctgtgct gtccctgcag ctctctttcc tctggtccaa | 1560 |
| atttcactat ctgtgatgct tcttctgacc cgtcatctca catttttccct tccccaaga | 1620 |
| tctagtgaac attcagcctc cattaaaaaa gtttcactgt gcaaatatat ctgctattcc | 1680 |

```
ccatactcta taatagttac attgagtgcc acataatgct gatacttgtc taatgttgag    1740
ttattaacat attattatta aatagagaaa gatgatttgt gtattataaa aaaaaaaaa    1799
```

PROFILING EXPRESSION AT TRANSCRIPTOME SCALE

CROSS-REFERENCE TO RELATED APPLICATIONS

This application is a continuation-in-part of U.S. application Ser. No. 14/480,525, entitled Attenuators, filed Sep. 8, 2014, the contents of which are incorporated herein in their entirety.

This invention was made with government support under grants 1R43HG007339-01 and 5R43HG007339-02 awarded by the National Institutes of Health. The government has certain rights in the invention.

TECHNICAL FIELD

This invention relates to molecular biology, and more particularly to assays for detecting nucleic acid sequences in samples.

SUMMARY OF THE INVENTION

This invention provides methods for detecting target nucleic acid sequences of interest in a sample, as well as methods for making detector oligonucleotides and kits comprising the detector oligos.

In a typical ligation assay, the sample is contacted with a pool of detector oligos, where a downstream detector (DD) and an upstream detector (UD) are provided for each target sequence. A portion (DR') of the DD is complementary to a region of the target sequence designated as a downstream region (DR). The upstream detector has a portion (UR') complementary to an upstream region (UR) of the target sequence. When downstream and upstream detectors are allowed to hybridize to the corresponding regions of the target sequence in a sample, the detector oligos can be ligated at the junction between adjacent detectors, optionally following an extension step. Formation of a ligation product thus serves as evidence that the target sequence was present in the sample, and the ligation product can be detected by various methods such as microarrays, qPCR, flow-through counters, and sequencing.

During hybridization, the DD and UD hybridize to the target molecule, but may hybridize to closely homologous molecules as well. Prior ligation assays relied on the selectivity of the hybridization and ligase steps to provide positive detection of target sequences. These may be insufficiently selective in the presence of sequences similar to the target sequences of interest, and limit the plexity of such assays to selectively detect more than 1000 target sequences in a single assay experiment.

This invention provides methods for identifying target sequence candidates (TSCs), which have DR' and UR' that are incorporated into downstream and upstream detector probes for a full-length sequence of interest. The TSCs are compared with other sequences that are potentially present in the sample. Based on match and mismatch patterns of the bases nearest to the ligation junction, TSCs are ranked and identified that are least likely to cross-react with other, off-target sequences and to eliminate potential false-positive results. The selectivity provided by the invention enables multiplex expression profiling, with minimal to no interference from off-target molecules, at the scale of the human transcriptome.

BRIEF DESCRIPTION OF THE DRAWINGS

FIGS. 3a-3f illustrate the use of detector oligos in a ligation assay to selectively detect a target sequence of interest. Throughout the figures, regions that are upstream in the direction of transcription (5'-direction of mRNA) are usually underlined to distinguish regions of similar length that are in the downstream (3') direction. The upstream and downstream designations are maintained for complementary oligos that are or can be hybridized to the mRNA, even if the upstream direction is in the 3'-direction of the complementary detector regions. Where positions are given within a SEQ ID NO, the order for the residues is given in the left-to-right direction as depicted in the figure, whether 5'-to-3' (as in detector oligos) or 3'-to-5' (as in mRNAs).

Middle FIG. 3b shows an mRNA of variant 1 of the human CYP2C8 gene (NM_000770.3 in the 3'-to-5' orientation) as an exemplary full-length sequence (FLS) of interest (SEQ ID NO:16 or residues 391 to 336 of SEQ ID NO:8) being shown as a representative 56-base partial sequence of CYP2C8 that is present in a sample. A 25-base downstream region (DR) of the CYP2C8 FLS is shown (residues 388 to 364 of SEQ ID NO:8), having three downstream ligation-sensitive bases (DLSB) as residues 366 to 364 of SEQ ID NO:8. A 25-base upstream region (UR) of the CYP2C8 FLS is shown (residues 363 to 339 of SEQ ID NO:8), having three upstream ligation-sensitive bases (ULSB) as residues 363 to 361 of SEQ ID NO:8. The bases of the DLSB and ULSB are often indicated in bold.

Figure 1:
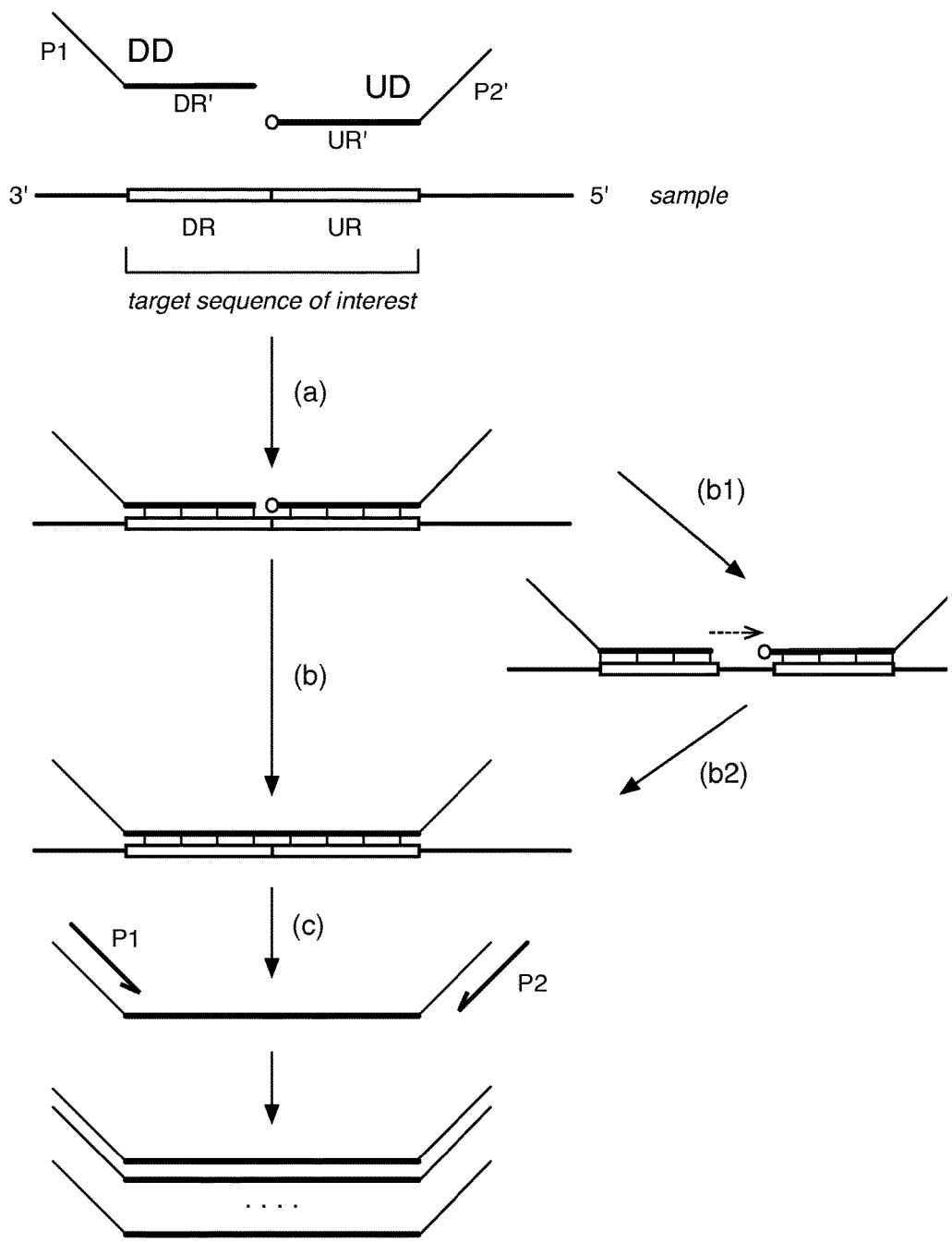
FIG. 1 illustrates a representative ligation assay for detection of target nucleic acid sequences. Briefly, downstream detector (DD) and upstream detector (UD) oligonucleotides are allowed to (a) hybridize to a target sequence of interest, having DR and UR regions, in a sample. The DD is (b) ligated selectively to the UR. Optionally, the DD is (b1) extended prior to (b2) ligation. The ligation product can be (c) amplified with one or more primers, such as P1 and P2. Note this lettering scheme for steps is used primarily for FIG. 1.

Shown partially hybridized to the DR of the FLS is a downstream detector oligo (DD) for TSC 32, which has a P1 region (SEQ ID NO:10) at the 5'-end and a sequence (DR', residues 388 to 366 of SEQ ID NO:8) that is complementary to the 25-base DR of TSC32. Partially hybridized to the UR is an upstream detector oligo (UD), which has a sequence (UR', residues 363 to 339 of SEQ ID NO:8) that is complementary to the 25-base UR, and a P2' region (SEQ ID NO:11) at the 3'-end of the DD. The DD and UD of TSC32 have adjacent 3 ligation-sensitive bases (LSBs CAT and TAT) in complementary alignment to the DLSB (gua) and ULSB (aua) of CYP2C8 mRNA. As shown, when the TSC32 downstream detector and TSC32 upstream detector hybridize to the DR and UR of the CYP2C8 mRNA, the 6 bases of the LSB of the detectors are perfectly complementary to the 6 bases of the combined DLSB and ULSB. Under appropriate ligation reaction conditions, the adjacent DR and UR (DR-UR or TSC32) serve as a template so that a ligase will successfully join the 3' end of the DD to the 5' end of the UD, indicated by the check mark. The product of the ligation reaction will be an oligonucleotide that has the form 5'-P1-DR'-UR'-P2'-3'. Detection of this ligation product indicates that the DR-UR, and hence target sequence TSC32 (as a representative subsequence of CYP2C8), was present in the sample.

FIGS. 3a and 3c illustrate situations where candidate TSC32 detectors hybridize to other sequences that are similar but not identical to target sequence TSC32. In FIG. 3a, CYP2C9 mRNA (SEQ ID NO:15 or residues 321 to 266 of SEQ ID NO:9, NM_000771.3), a similar full-length sequence (SFL) to CYP2C8, is provided having about 83% identity with CYP2C8. The downstream TSC32 detector is shown hybridized to the corresponding DR of CYP2C9 (residues 318 to 294 of SEQ ID NO:9), and the upstream TSC32 detector is shown hybridized to corresponding UR of CYP2C9 (residues 269 to 293 of SEQ ID NO:9). While most of the DR' and UR' of the CYP2C8 detectors are complementary to the DR and UR of similar CYP2C9, the ligation-selective bases of TSC32 (TSC-LSB) have critical mismatches with the LSB of similar SFL CYP2C9. As provided by the invention, ligation of the TSC32 DD and UD will not occur due to the mismatches in the LSB; thus, the TSC32 detectors for CYP2C8 would not produce a misleading ligation product in the presence of CYP2C9 mRNA. Similarly, FIG. 3c shows a CYP2C19 mRNA (SEQ ID NO:17 or residues 321 to 269 of SEQ ID NO:19) as the SFL (82% identity to CYP2C8), where the TSC32 detectors for CYP2C8 have a TSC-LSB that is dissimilar to the LSB of the SFL, CYP2C19. Thus, the CYP2C19 mRNA, if present in a sample, would not yield a false-positive ligation product from the TSC32 detectors for CYP2C8.

FIG. 3d is similar to FIG. 3a, except the LSBs are asymmetrical relative to the ligation junction: the DLSB is 4 bases and the ULSB is 1 base. In this probe design, the 26-base DR' is residues 388 to 363 of SEQ ID NO:8, and the 24-base UR' is residues 362 to 339 of SEQ ID NO:8. The TSC-LSB is 5'-CCAT_T_-3' (residues 366 to 362 of SEQ ID NO:15), and the analogous SFL-LSB is 3'-gguu_c_u-5' (residues 32 to 28 of SEQ ID NO:15).

FIG. 3e shows a probe design similar to FIG. 3b, except the DR' is shorter at the 3' end by two bases (thus, residues 388 to 366 of SEQ ID NO:8). The ligation-selective bases are the three 5' bases of the UD, marked as TSC-LSB (residues 363 to 361 of SEQ ID NO:8). When an extension step is used in the assay (such as step (b1) in FIG. 1), the DD is extended along the CYP2C8 template by adding bases A and T, providing adjacent bases for selective ligation to the UD.

FIG. 3f is similar to FIG. 3c, but illustrates detector oligos having locked nucleic acids in the TSC-LSB, indicated by the =s.

FIGS. 4a, 4b, 4c, 4d, and 4e provide examples of adjacent 25-base DR' and 25-base UR' detector sequences of TSCs for CYP2C8 with comparison to the CYP2C8 mRNA sequence (rectangle), and as well as comparison to analogous regions of CYP2C9 (SEQ ID NO:9), CYP2C18 (SEQ ID NO:18), and CYP2C19 (SEQ ID NO:19), with residues marked as NM positions. Match scores are provided for each TSC for the most similar full-length sequences (SFL).

FIG. 5 shows the attenuated detection of the target sequence GAPDH_2 when using various combinations of mutated downstream attenuators and mutated upstream attenuators.

FIG. 5a re-presents the attenuated ligation frequencies in FIG. 5 as match scores for various combinations of 1-, 2-, and 3-base downstream matches (DLSB) with 1-, 2-, and 3-base upstream matches (ULSB) for the LSB of a given FLS. FIGS. 5b and 5c show two of the many possible alternate match scorings for the values in FIG. 5.

FIG. 6 shows TSCs designed to match the junctions between 6 exons of CYP2C8 (SEQ ID NO:8), and with comparison to analogous regions of CYP2C18 (SEQ ID NO:18) and CYP2C19 (SEQ ID NO:19) as SFLs. For each junction, match scores according to FIGS. 5a, 5b, and 5c are provided, as well as the % GC of the downstream probe DR' and upstream probe UR', and a composite % GC score.

FIG. 7a is a profile of 188 TSCs for CYP2C8 where % GC was the sole prioritization parameter, and priority is shown on an arbitrary 0-1000 scale. FIG. 7b shows a comparable profile for the TSCs using pattern Match Scores of the invention. FIG. 7c shows an example of a profile for the TSCs in FIG. 7b with additional penalty considerations discussed herein.

DETAILED DESCRIPTION OF THE INVENTION

This invention provides methods for detecting target nucleic acid sequences of interest in a sample. The sample can be any substance where it is desired to detect whether a target sequence of a nucleic acid is present. Such samples can be from living or dead organisms, or from artificially created or environmental samples. The samples can be from humans, nonhuman animals, plants, yeast and other microorganisms, prokaryotes, or cell lines thereof. The samples can be in the form of tissue samples, cell samples, or samples that are cell-free. The samples can be provided in liquid phase, such as cell-free homogenates or liquid media from tissue cultures, or in solid phase, such as when the sample is mounted on a slide or in the form of formalin-fixed paraffin-embedded (FFPE) tissue or cells.

The target nucleic acid sequence of interest to be detected in a sample can be a sequence or a subsequence from DNA, such as nuclear or mitochondrial DNA, or cDNA that is reverse transcribed from RNA in the sample. The sequence of interest can also be from RNA, such as mRNA, rRNA, tRNA, miRNA, siRNAs, antisense RNAs, or long noncoding RNAs. More generally, the sequences of interest can be selected from any combination of sequences or subsequences in the genome or transcriptome of a species or an environment.

For some sample types, the number of target nucleic acid sequences of interest can range in any combination of upper and lower limits of 1, 2, 5, 10, 20, 50, 100, 200, 500, 1000, 2000, 5000, 10,000, 20,000, 23,000, 30,000, 38,000, 40,000, 50,000, or more. The number of target sequences of interest can also be expressed as a percentage of the total number of a defined set of sequences, such as the RNAs in the human transcriptome or genes in the human genome, ranging in any combination of upper and lower limits of 0.1%, 0.2%, 0.5%, 1%, 2%, 5%, 10%, 20%, 25%, 30%, 35%, 40%, 45%, 50%, 65%, 60%, 70%, 75%, 80%, 85%, 90%, 95%, and 100%. The defined set can have at least 500, 1000, 2000, 5000, 10,000, 20,000, 30,000, 40,000, or 50,000 sequences.

Ligation Assays

While many methods can be used to detect the presence of a target sequence, a representative method is a ligation assay, such as in Example 1 and illustrated schematically in FIG. 1. In a typical ligation assay, the sample is contacted with a pool of detector oligonucleotides ("detectors"). For each target sequence of interest, a pair of detectors is provided: a downstream detector (DD) and an upstream detector (UD). A downstream detector can have a portion (DR') that is complementary to a region of the target sequence designated as a downstream region (DR). An upstream oligo can have a portion (UR') that is complementary to a region of the target sequence designated as the upstream region (UR). Here, the terms "downstream" and "upstream" are used relative to the 5'-to-3' direction of transcription when the target sequence is an mRNA. The DR and UR of a target sequence are typically subsequences of the entire target sequence of interest, and an individual target sequence can have more than one set of DRs and URs, which can be selected by the user to optimize the performance of the assay. Multiple sets of DRs and URs can provide multiple measurements of the same target sequence or of different portions of the target sequence, such as different exons or exon junctions, or provide measurement of a portion of sequence that is not mutated versus a portion of sequence that may harbor a mutation.

In many target sequences, the DR and UR are directly adjacent; in others, they can be separated by one or more nucleotide positions on the target sequence, as in FIG. 3e. Accordingly, an extension step (b1) can be performed, as shown in FIG. 1, followed by the ligation step (b2) described in more detail below.

The DD or UD, or both, can contain a barcode sequence. For example, a useful barcode sequence can uniquely identify the specific gene or target sequence, or a group of select genes or target sequences within the sample that are being measured. Such sequences can be positioned between the UR' and P2' sequence, and/or between the DR' and P1 sequence, so they are amplified when using flanking primers. This sequence can also be a random sequence, useful for identifying the number of copies of the target gene in the sample, independent of the efficiency of any amplification.

In a ligation assay, the pool of detector oligos is contacted with the sample. As shown in FIG. 1, the DR' of the DD and the UR' of the UD for each target sequence are allowed to hybridize (a) to the corresponding DR and UR of the target sequence, if present in the sample, serving as a template.

When the DR and UR of a target sequence are directly adjacent, the detector oligos can be ligated (b): thus formation of a ligation product serves as evidence that the target sequence (DR+UR) was present in the sample. The ligation reaction can occur by chemical ligation or by using a ligase enzyme. A variety of nick-repairing ligases are commercially available to catalyze the formation of a phosphodiester bond between adjacent single-stranded polynucleotides when hybridized to another single-stranded template. An example is bacteriophage T4 DNA ligase, which uses ATP as a co-factor. The ATP can be supplied during the ligase reaction. In other reactions, the ligase can be pre-adenylated. In other reactions, the UD must be pre-adenylated at the 5' end, as with a 5' App DNA/RNA ligase. The UD in a typical reaction will have a 5'-phosphate to facilitate ligation to the DD, although this is not necessary, depending on the selection of ligase and ligation conditions. Where a 5'-phosphate on the DD is required for efficient ligation, using a comparable oligonucleotide without 5'-phosphorylation can be used to inhibit ligation.

The detector oligos be DNA, RNA, or a mixture of both. If desired, they can have a modified nucleotide such as dideoxy nucleotides, deoxyUridine (dU), 5-methylCytosine (5mC), 5-hydroxymethylCytosine (5hmC), 5-formylCytosine (5fC), and 5-carboxylCytosine (5caC), and Inosine. Yet other modifications to detector oligos include modified bases such as 2,6-diaminopurine, 2-aminopurine, 2-fluro bases, 5-bromoUracil, or 5-nitroindole.

Ribonucleotides can be substituted at the ligatable ends of the DD and UD to increase the specificity and efficiency of ligation, as when an RNA ligase is used. The modified bases can also be used at positions 1, 2, or 3 away from the point of ligation.

Other detector oligos can have a modified a sugar-phosphate backbone at one or more positions. Such modifications include a 3'-3' or 5'-5' linkage inversion, a locked nucleic acid (LNA), or a peptide nucleic acid (PNA) backbone. In FIG. 3f, for example, LNAs are shown in the LSBs of the DD and UD, and can be useful for their stronger hybridization properties to complementary bases, enhancing the selectivity in a TSC-LSB or the overall binding affinity for the detector oligo as a whole.

It can be desirable for a detector oligo to contain one or other modifications that can be cleaved by treatment after the ligation or optional amplification step. For example, a detector oligo can have a dU located so that it will not interfere with hybridization or ligation steps. After ligation, however, products incorporating the dU oligo can then be cleaved by dU-specific enzymes, such as uracil-DNA glycosylase followed by endonuclease VIII.

Another approach is to incorporate into a detector oligo a selectively cleavable site so that it can be cleaved without affecting the other components of the assay. A selectively cleavable site can be a restriction enzyme cleavage site that is not present in the target sequences of interest to be detected. The sample can be pre-treated to remove undesired target sequences, for example by using immobilizable beads or other solid phase that contain oligonucleotides that are specifically complementary to undesired sequences. Beads to remove rRNA and globin sequences are commercially available. If a capture sequence on a solid phase surface hybridizes to the UR and/or DR, or a portion of either, then including the capture sequence with the DD and UD at a predetermined ratio can deplete a portion of the sequence. Similarly, an oligo that targets the UR and/or DR or a portion of one or both—and that in turn can be captured onto a surface through a second sequence—can be used to compete with the DD and/or UD. Then, the sequence—to which the competitive, capturable oligonucleotide is hybridized—can be removed from the sample. One skilled in the art will see that there are many combinations that can be used for selective capture and depletion of undesired sequences in a sample.

Ligation can be preceded by a cleavage step, such as by a nuclease, to remove any overhangs. In other cases, a portion of the DD can overlap with the UR sequence to which the UD hybridizes, so that after hybridization of the UD and the DD, there is an overhang sequence of 1, 2, 3, or more bases. A useful enzyme for removing an overhang is a Flap endonuclease, such as FEN-1.

Where the ligation assay proceeds directly to a detection step, either or both detectors can be designed to be labeled appropriately for detection. For example, the detector can be labeled with a color or fluorescent dye, latex bead, quantum dots, or nanodots. The label can also take the form of an additional nucleotide sequence that serves to enable detection and identification, such as a barcode sequence.

In some embodiments, the hybridization, ligation, or extension steps can be performed while the target sequence is in situ. This can be particularly useful, for example, when the sample is on histological slide, so that the ligation is known to occur at a recordable location and can be compared to similar reactions at other locations on the slide. In a particular embodiment, the ligation products can be eluted from the sample in situ for collection and further processing, preferably eluting from small areas to preserve the location information of the ligation reaction products.

In some assay formats, the ligation products can be (c) amplified to facilitate detection. As illustrated in FIG. 1, the detectors can have additional sequences ("tails") including primer hybridization sequences (e.g. P1, P2') or complements thereof, that serve as amplification sequences, so that after ligation, the ligation product can be amplified with a pair of amplification primers (P1, P2). An exemplary downstream amplification sequence (P1) is (SEQ ID NO: 10)
5'-CAAGCAGAAGACGGCATACGAG-3', which can be used with a primer having the same sequence (P1). An exemplary upstream amplification sequence (P2') is (SEQ ID NO: 11)
5'-ATCTCGGTGGTCGCCGTATCATT-3', which can be used with primer P2 (shown in 3'-to-5' orientation):

(SEQ ID NO: 12)
3'-TAGAGCCACCAGCGGCATAGTAA-5'.

If desired, the amplification primer can incorporate a barcode sequence, for example a barcode sequence that uniquely identifies the sample in a multi-sample experiment. The barcode sequence can be incorporated into the primer, such as 3' to the amplification sequence, so that the barcode becomes part of the amplified strand. In other instances, the amplification sequence of the primer can be extended by an additional sequence to provide a primer hybridization sequence that can be used for use in subsequent sequencing steps. The barcode may also be interposed between the amplification sequence, and if desired, the extended amplification sequence, and another sequence that can be used for capture, such as capture onto a surface as part of a sequencing process, and/or for yet another primer hybridization sequence that is used for sequencing. In each case the barcode will be amplified with the rest of the detector sequences, for instance forming a single amplified, elongated molecule that contains sequencing primer hybridization sequences, sample barcode, and a gene-specific sequence, which may include a gene-specific barcode or a target molecule-specific barcode as well as sequence or complement to the sequence of the target gene. In the case where the targeted oligo is a cDNA, a gene-specific sequence or a sample specific sequence can be added as part of the primer used for reverse transcription, and be a part of the sequence targeted by the UD and DD.

In other instances, methods known in the art can be used to amplify the ligated DD and UD sequences, such as by repetitive cycles of (1) ligation, (2) heating to melt off the ligated product, (3) cooling to permit hybridization of DD and UD to the target, (4) ligation, then repeating the heating (2), cooling (3), and ligation (4) steps. These additional amplification steps can be performed before amplification step (c), during which the sample barcodes and other sequences are added to the ligated UD and DD sequence. The target of the UD and DD hybridization may also be amplified by whole transcriptome amplification of RNA or amplification of cDNA.

The ligation product (or its amplicons) can then be detected by methods such as sequencing, qPCR, or labeling for detection on an array or other molecule detection. Other detection methods include flow-through systems for counting labeled molecules. Depending on the detection method, the skilled user will be able to modify the design of the detectors and amplification primers to include functional features that are appropriate, such as for bridge amplification on a sequencing flow cell.

Attenuators

To provide context for the assays of the invention described herein, various attenuator oligonucleotides ("attenuators") can be used to attenuate the overall number of ligation or amplification products to be detected. Some attenuators are provided that can replace one or both of the detectors for highly abundant target sequences (HATs) to provide positive detection of the HAT in the sample, but at a lower level of signal. These and other attenuators can also be added to the ligation reaction to attenuate the signal for the HATs.

Attenuators can hybridize competitively with part or all of a DR and/or UR of a HAT. A downstream attenuator can hybridize to a portion of a DR, reducing access of a corresponding DD to the same DR. Similarly, an upstream attenuator can hybridize competitively to a portion of an UR. As with all detector oligos and attenuators disclosed herein, the length and sequence of the oligonucleotide can be tuned for desired properties such as specificity, and annealing and melting temperatures. For example, an oligo may be tuned to increase or decrease the number of C:G pairs formed during hybridization steps of the assay.

An embodiment of attenuator oligonucleotide that can replace a detector can have a portion partially complementary to the downstream or upstream region of the HAT. A particular embodiment is when the attenuator has a sequence similar to a detector, but has one or more mutated positions. Examples of such mutated attenuators are described in Example 2. Some mutated DDs have one, two, or three mismatches (relative to the DR template) at positions at or near the 3' end. Some mutated UDs have one, two, or three mismatches (relative to the UR template) at positions at or near the 5' end. A mutated DD can be used in combination with an unmutated ("wildtype") UD; a mutated UD can be used with a wildtype DD; or various mutated upstream and downstream detectors can be combined, depending on the degree of attenuation desired. Moreover, a mutated attenuator for a HAT can also be useful when provided during hybridization in addition to the wildtype detectors for the same HAT. The net result is to optimize the utilization of assay and detection resources among HATs and the other target sequences of interest. The use of attenuators is particularly effective when the relative number of amplification products for other target sequences of interest is maintained, and preferably enhanced.

Ligation-Selective Bases (LSBs)

The relative ligation efficiencies described in Example 2 and shown in FIG. 5 are for various combinations of oligonucleotides when hybridized to a template sequence. Because the bases of the internal sequence at the ligation junction have one or more salient mismatches to the template, the bases are termed ligation-selective bases (LSBs). When the oligonucleotides are perfectly complementary to the target sequence of interest (LSBs having a match pattern with the template of IIIIII) the ligation efficiency is 100%, as a trivial case. When the template has mismatches with the LSBs, however, the ligation efficiency can decrease, as would be the case when a similar but nonidentical sequence is present and serves as a template. When the LSBs of detector oligos for a target sequence have patterns of one or more mismatches (X) to comparable bases of a nonidentical template, the ligation efficiency is decreased according to FIG. 5. Accordingly, methods are provided herein for reducing the ligation efficiency of target detector oligos when hybridized to non-target templates.

The present invention provides methods for selecting candidate nucleotide sequences for designing detector oligos to detect the presence of one or more full-length target sequences of interest (FLS) in a sample. When detecting a full-length sequence, the entire sequence can be detected directly, or it can be useful to select a representative subsequence for detection, here designated the target sequence (TS). When several TSs are being considered to serve as the TS for use as detectors in the assay, they can be described as target sequence candidates (TSCs). The TSC provides the sequence for the downstream region (DR) and upstream region (UR), the complements of which will be the DR' and UR' of the detector oligos.

A TSC can be of any length, but preferably has enough bases so the complementary DR' and UR' will hybridize to the target sequence under conventional hybridization conditions, such as provided in Example 1.

The detector oligos derived from a TSC may contain non-naturally occurring bases or nucleotides, such as locked nucleic acids or peptide nucleic acids, to increase base-to-base hybridization specificity, as in FIG. 3*f*. The TSC can have a DR and UR of the same length, such as 20b+20b, or unequal lengths, such as 26b+24b in FIG. 3*d*. Useful TSCs can be any length between 14 and 100 bases in length, and include 40 bases (for a 20-base DR and 20-base UR) and 50 bases (for 25-base DRs and UR5). If a full-length target sequence of interest (FLS) is 100 bases, for example, there are 51 possible TSCs of 50 bases each, starting with TSC1 (bases 1-50), TSC2 (bases 2-51), TSC3 (bases 3-52), to TSC51 (base 51-100). Where a TSC is an mRNA, it is often described herein in the 3'-to-5' direction from left to right, so TSC51 can be described as residues 100 (left, downstream) to 51 (right, upstream) of a particular full-length sequence. Naturally, many FLSs of interest in a sample can be much longer or much shorter than 100 bases, and final the length of the TSC and probes depend on the hybridization conditions to be used, the specificity desired, and the selectivity intended when similar sequences may be present.

As discussed above, when an extension step is incorporated into the assay, the 3' bases of the DD are extended along the sample template. In this case, identification of a DLSB is unnecessary, and the TSC-LSB can be the ULSB alone, as in FIG. 3. Nevertheless, the sensitivity of the ligase to mismatches near the junction site provide an additional layer of selectivity in case of mis-incorporated bases during extension.

The DR of a TSC has zero, one, or more ligation-selective bases (LSB) at the 3'-end (DLSB). The DLSBs can be a single (as in the -I and -X of FIG. 5*a*), two bases (-II, -XI, -IX, -XX), three bases as discussed more fully herein, or 4, 5, 6, 7, 8, 9, or 10 bases or more. The UR of a TSC has one or more ligation-sensitive bases at the 5'-end (ULSB). The ULSB also can be a single base (p-I-, p-X), two bases (p-II-, p-IX-, p-XI-, p-XX-, three bases, or 4, 5, 6, 7, 8, 9, or 10 bases or more. The p-indicates an optional phosphorylation at the 5'-end of the UR' to promote ligation. The length of DLSBs and ULSBs need not be equal, so that Tables 5a, 5b, and 5c can be readily used for combinations of 2-base DLSBs and 3-base ULSBs. In FIG. 3*d*, for example, the LSBs are a 4-base DLSB and a one-base ULSB. If desired, the lengths of the DLSB and ULSB can be tuned empirically to provide a desired degree of selectivity where members of the defined set are highly homologous. Such selectivity can be tuned for individual targets of greater than 80%, 85%, 90%, 95%, 97%, 98%, 99%, 99.5% or 99.9% compared to similar off targets.

Collectively, the DLSB and ULSB are described as the LSB, and when the LSB of a TSC, the abbreviation TSC-LSB is sometimes used. For each TSC, a search is performed against other sequences in the defined set of sequences to find similar sequences according to predetermined criteria. The defined set can be the universe of sequences that would be expected in a sample, for example a genome or transcriptome, or a smaller set when the sequences are known and well-characterized, such as from an artificial source. The defined set can also be virtually unlimited, as with an environmental sample, hence any available database. Nevertheless, the search is performed by sequence similarity to the extent available. Numerous search methods are available, such as blastn (nucleotide-nucleotide BLAST) used in Example 5. Other algorithms and heuristic methods include FASTA, BLAT, KLAST, SSEARCH, PSI-SEARCH, GGSEARCH, GLSEARCH, megablast, provided on the website of the National Center for Biotechnology Information (NCBI), WU-BLAST, PSI-BLAST, or the European Nucleotide Archive (ENA) sequence search. Preferably the search provides a local alignment to a complementary similar full-length sequence (SFL). The SFL need not be the most similar sequence to the TSC, but should be similar according to objective criteria selected by the user.

Based on the alignment of the TSC to the SFL, a set of complementary bases in the SFL, corresponding to the ULSB and DLSB of the TSC are defined as the LSB of the SFL (SFL-LSB). As worked through in Example 5, FIG. 3*b* provides a trivial example where the FLS is CYP2C8 (SEQ ID NO:8) and the most similar SFL is CYP2C8 itself with 100% sequence identity. This figure represents upstream and downstream CYP2C8 detector oligos that are hybridized to CYP2C8 mRNA in a sample. The DLSB is 3'-gua-5' and the ULSB is 3'-aua-5' for a combined TSC-LSB of 3'-gua<u>aua</u>-5'. The target sequence candidate being considered in FIG. 3*b* has a 50-base sequence of CYP2C8, with a TSC-LSB of 5'-CAT<u>TAT</u>-3'. A downstream detector based on this TSC will have a P1 portion and a DR' with -CAT at the 3' end. The upstream detector will have a UR' with p-<u>TAT</u>- at the 5' end and a P2' portion. When the upstream and downstream detectors are hybridized to the CYP2C8 mRNA, the detectors will be adjacent and the LSB-TSC will be perfectly complementary to the DLSB+ULSB, allowing a ligase to join the two detector oligos, indicated by the check mark in FIG. 3*b*.

In a sample, the same detectors can be exposed to mRNAs that are slightly different in sequence but biologically significant, such as closely related CYP2C9 (SEQ ID NO:9) and CYP2C19 (SEQ ID NO:19), which serve as potentially confounding similar full-length sequences (SFLs) in FIGS. 3*a* and 3*c*. In these figures, the LSB-TSC and LSB-SFL are not perfectly complementary. While a ligase may be tolerant of certain mismatches, not all mismatch patterns result in ligation. In these figures, the detector oligos readily hybridize to the SFLs, but the mismatched bases at the junction between the detectors prevent ligation, indicated by Xs. If the detectors were to be ligated, this may lead to reporting of a false positive detection of CYP2C8 in the presence of CYP2C9 or CYP2C19 in a sample. However, the lack of ligation from the pattern of mismatched bases prevents the false positive result, even in the presence of highly similar SFLs in the sample. Thus, the LSB differentiates target molecule from closely homologous (off-target) molecules, and reduces or prevents ligation when hybridized to the off-target molecules.

The dissimilarity of LSBs in a TSC (being considered for a FLS) and an SFL (as identified by the search and alignment) can be described by FIGS. 5a, 5b, and 5c. The frequency of ligation for each match pattern is represented by a Match Score (MS) of 0.1 to 0.9. A low MS indicates that the TSC-LSB and SFL-LSB are too similar and would yield poorly selective probes that risk false-positive results. A high MS indicates the TSC-LSB and SFL-LSB are sufficiently mismatched that ligation is unlikely, and the probes designed from the TSC would be highly selective against similar sequences in the sample. Application of the Match Scoring is worked out in detail in Examples 3 and 4.

An optional Match Score of 1.0 can be assigned where a TSC is sufficiently dissimilar from all other sequences according to the predefined search criteria. Representative scores for TSCs are shown in FIG. 7c.

Figure 2:
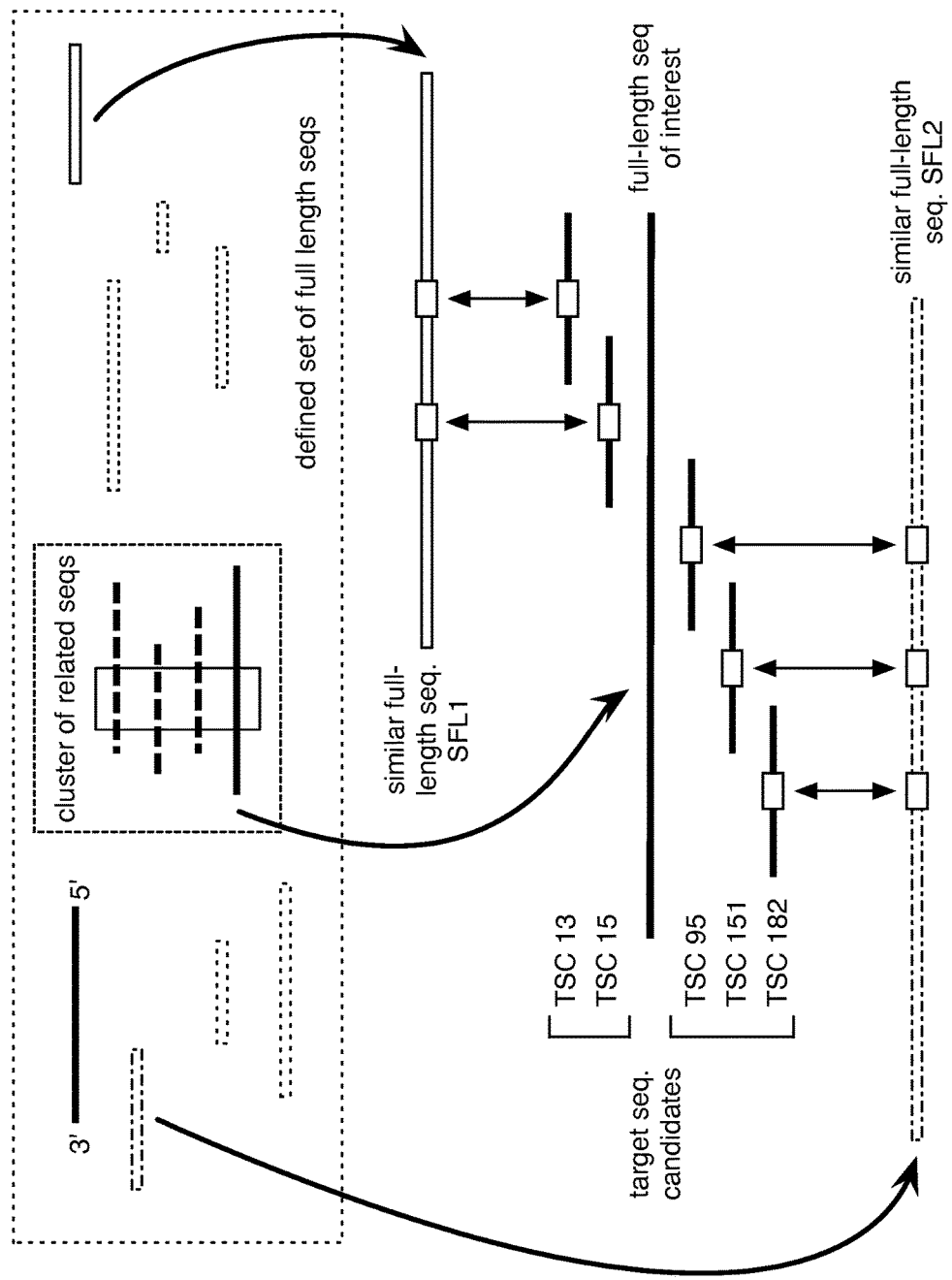
FIG. 2 illustrates the evaluation of target sequence candidates (TSCs), which are subsequences of a full-length sequence of interest (FLS). The FLS is member of a defined set of full-length sequences, where the set is indicated by the dotted rectangle. In some embodiments, a cluster of related sequences (isoforms) is further defined, indicated by the dashed rectangle. Various TSCs of the FLS are compared with similar subsequences of other full-length sequences (SFL1, SFL2) from the defined set. In this figure, TSC 13 and TSC 15 are compared with analogous regions of SFL1. Comparisons are also shown between TSC 95, TSC 151, and TSC 182 and analogous regions of SFL2. Ligation-selective bases (LSBs) are indicated schematically by the small boxes in the TSCs and SFLs.

As another optional step, where some full-length target sequences are sufficiently related to the full-length sequence of interest, they can be considered a cluster of related sequences (isoforms), as shown in FIG. 2. Within a cluster, an FLS can be the shortest or longest sequence, the sequence having the most shared sequence with the other isoforms, the sequence with the most exons, or the sequence with the greatest or least homology or % identity to the other isoforms. When a search is performed for each TSC, the other members of the cluster are excluded from being considered an SFL in generating the match scores. TSCs can be weighted and prioritized according to the frequency of their presence in the members of the cluster.

The TSCs can be further prioritized by applying additional criteria. For example, ligation efficiency can be reduced if the base at the 3'-end of the junction is guanine. In one embodiment, a penalty factor (0.0, 0.1, 0.2, 0.3, 0.4, or 0.5 for example) can be applied to the Match Score of a TSC that would result in such an upstream detector. Other penalty factors can be applied for other bases in that position, for example favoring thymine, cytosine, and then adenine, ranging from 1.0, 0.9, 0.8, 0.7, or 0.6, for example.

Another factor is to favor a TSC according to its proximity to the 3'-end of the FLS. Thus, a multiplying factor can be applied, such as

| distance of 3'-end of TSC to 3'-end of FLS | factor |
| --- | --- |
| 0-25 bases | 0.7 |
| 26-500 bases | 1.0 |
| 501-800 bases | 0.9 |
| 801-1100 bases | 0.8 |
| 1101-1500 bases | 0.7 |
| 1501-2000 bases | 0.6 |
| 2001-3000 bases | 0.3 |
| 3001+ bases | 0.1 |

Other factors include penalizing a TSC that has homopolymeric runs of varying length. Examples of factors are

| consecutive bases: | factor |
| --- | --- |
| 2 | 1.0 |
| 3 | 0.7, 1.0 |
| 4 | 0.1, 0.4, 0.7 |
| 5 | 0.1, 0.4, 0.7 |
| 6 | 0.0, 0.1, 0.4 |
| 7 | 0.0, 0.1 |

TSCs can also be penalized for repeated multinucleotide sequences, such as dinucleotide or trinucleotide sequences, such as various combinations of factor 0.1 for 5, 6, or 7 or more repeated dinucleotides, factor 0.5 for 3 to 7 repeats, and factor 1.0 for 4, 3, 2, or 1 repeats. Similarly, repeated runs of any two bases can be penalized, such as runs of pyrimidines in the mRNA. As an example, more than 13 contiguous Ts or Cs in a 50-base mRNA (or Gs or Cs in either 25-base detector probe) can be penalized by a factor of 0.5 or 0.1. A tool to remove simple repeats, such as RepeatMasker, can also be used deprioritize TSCs and detectors.

Depending on the target sequence of interest and the complexity of the sample, it can be desireable to include a penalty factor for target sequences that are similar to repeated RNA and DNA sequences that are known to be present in the sample. Other sequences that can be deprioritized include known rRNAs, miRNA, non-coding RNAs, and any other sequence where attenuation is desired.

It may also be desireable to include a penalty or proportional correction factor when the target sequence is previously known to be present in two or more copies within a full-length sequence of interest, or in multiple copy numbers within the genome of the sample. It may also be desirable to prefer a TSC that selectively detects repeated sequences, for example to multiply the sensitivity of the assay for that target sequence. Alternately, fine-scale recombination may be detected by comparing the ration of detection of target sequence with potential repeats to a target sequence for the same gene or sequence without known repeats.

Other tools can be applied to further prioritize the TSCs. Where a FLS has known single-nucleotide polymorphisms (SNPs) of varying frequency, it can be desireable to avoid detector oligo designs that target only rare SNPs, such as SNPs having a minor frequency allele (MAF) less than 5%, 2%, 1%, 0.5%, 0.2%, 0.1%, 0.05%, 0.02%, or 0.01% on a database such as dbSNP.

Yet another factor is the % GC (guanine and cytosine) of the TSC or the individual detectors. Representative penalty factors are

| % GC ranges | factor |
| --- | --- |
| 40-60 | 1.0 |
| 35-39 or 61-65 | 0.7 |
| 25-34 or 66-75 | 0.4 |
| 0-24 or 76-100 | 0.1 |

One or more of the factors described above can be applied to obtain an overall priority for each TSC among the possible TSCs for an FLS. The individual factors can be scaled to a common range to facilitate comparison. The factors can be added or multiplied in various mathematical combinations, with optional exponentiation to emphasize or de-emphasize parameters of interest. For example, a complete, aggregated score that takes the penalties into consideration may be obtained by the general product $$a^i \times b^j \times c^k \times d^l \times e^m \times f^n \times \ldots$$

where a, b, c, d, e, and f etc. are individual parameters (such as pattern Match Score, % GC content) and i, j, k, l, m, and n etc. are exponents with a typical value of 1, but can be 0.25, 0.5, 1.5, 2, 3, 4, or their negatives, if desired.

The contribution of the pattern Match Score of 188 TSCs for CYP2C8 can be seen in FIG. 7b, and an exemplary profile of complete scores is shown in FIG. 7c, which can be compared to a profile obtained from % GC scores alone in FIG. 7a.

Accordingly, the present invention provides a method for prioritizing and selecting a target sequence of a FLS in a defined set.

The invention also provides a method for selectively detecting a plurality of target nucleic acid sequences of one or more FLSs in a sample by contacting the sample with pairs of detector oligos, ligating the DD and UD if both are hybridized to the DR and UR of a target sequence in the sample. An optional extension step can precede the ligation step. The ligation product indicates detection of the target sequence that is selective over SFLs in the sample.

The invention further provides methods for making the prioritized detector oligos for a FLS by conventional methods of synthesis.

This invention also provides sets of detector oligonucleotides described above. The set can be specific for a sample type, such as a cell or tissue type. This invention further provides kits containing the detector oligos. The kits and methods of the invention can include oligos in a range of any combination of upper and lower limits of 1, 2, 5, 10, 20, 50, 100, 200, 500, 1000, 2000, 5000, 10,000, or more target sequences of interest. Where large sets of detector oligos are used, it can be useful to check the full sequence of each oligo for potential cross-hybridization to other oligos in the set, where, for example, one oligo may serve as an template to other detectors. While such non-specific artifacts can be identified by sequence, and are typically discarded from detection results, they may represent noninformative hybridization events that compete for reaction resources. To reduce formation of nonproductive secondary structures during the hybridization and ligation steps, a BLAST or other similarity search can be used to search for reverse complementarity of 4, 6, 8, 10, 12, 14, 16, 18, 20, or 22 or more bases with the other oligos that may be present in a reaction. A problematic detector oligo for an FLS can then be removed from the set, and another TSC, DR, or UR selected for the FLS.

The kits can be provided with ligases and/or polymerases for use with the detector oligos. The kits can also have eluent solutions suitable for removing oligonucleotides, such as ligated oligonucleotides, from a tissue sample for further analysis. The kits can further have amplification primers suitable for use with the detectors of the kit.

EXAMPLES

Example 1: Representative Ligation Assay

A representative method is provided to illustrate ligation assays without the attenuators of the invention. Here, over 100 RNA expression products were detected in a sample of cells using a multiplex assay format. For each expression product, the assay was designed to detect one or more sequences of interest within the full sequence of the product. For example, in human cells, a GADPH gene encodes the enzyme glyceraldehyde 3-phosphate dehydrogenase; three different sequences of interest within the RNA transcript of the GADPH gene were independently detected. One such RNA sequence, identified here as GADPH_2, was (SEQ ID NO: 1)
5'-CGACCACUUUGUCAAGCUCAUUUCCUGGUAUGACAACGAAUUUGGC
UACA-3' where a 5' end was designated "upstream" (underlined) and the 3' end was designated "downstream" for the direction of transcription and translation. The same GADPH_2 sequence can be shown in the 3'-to-5' direction for later convenience of discussion:

(SEQ ID NO: 1)
3'-ACAUCGGUUUAAGCAACAGUAUGGUCCUUUACUCGAACUGUUUCAC
CAGC-5'

A downstream region (DR) was defined as the downstream 25 bases of GADPH_2:

(SEQ ID NO: 2)
3'-ACAUCGGUUUAAGCAACAGUAUGGU-5' which has a complementary DNA sequence of DR':

(SEQ ID NO: 3)
5'-TGTAGCCAAATTCGTTGTCATACCA-3'

The upstream region (UR) was defined as the upstream 25 bases of GADPH_2:

(SEQ ID NO: 4)
3'-CCUUUACUCGAACUGUUUCACCAGC-5' which has a complementary DNA sequence of UR':

(SEQ ID NO: 5)
5'-GGAAATGAGCTTGACAAAGTGGTCG-3'

For GADPH_2, a pair of detectors was designed: a downstream detector (DD) having the DR' sequence, and an upstream detector (UD) having the UR' sequence. Similar pairs were designed for each of the target sequences of interest to provide a pool of detectors for the assay. In this example, all the upstream detectors were phosphorylated at the 5' end.

In this particular example, an amplification step was to be performed later in the experiment using two primers, P1 and P2, so all UDs in the experiment included a primer sequence (P1) and all URs included a complementary primer sequence (P2'). Because amplification is not necessary to the practice of the invention, however, the sequence of the specific primers and primer sequences is a matter of selection to suit the particular amplification method, if used.

At least 10 ng of RNA isolated from human kidney or liver cell lines was placed in a well of a microtiter plate for each assay experiment. To each well was added 20 μL of 2× Binding Cocktail, which contained 5 nM of each detector (providing a final input of 0.1 pmoles per oligo), 100 nM biotinylated oligo(dT)$_{25}$, and 5 μL streptavidin-coated magnetic beads in a Wash Buffer (40 mM Tris-Cl pH 7.6, 1 M NaCl, 2 mM EDTA disodium, 0.2% SDS).

The plate was heated for 10 min at 65° C. to denature the RNA, then the temperature was ramped down over 40 min to 45° C. to allow the detectors to anneal to the RNA sample. The plate was then transferred to a magnetic base to immobilize the beads, allowing the supernatant, containing unbound and excess detectors, to be aspirated from the wells. The beads were washed at least three times with 50 μL Wash Buffer.

To each well was added 5 Weiss units of T4 DNA ligase in 20 μL of 1× ligation buffer, as provided by the supplier. After the beads were resuspended by pipette, the plates were incubated for 60 min at 37° C. to allow template-dependent ligation of DDs to UDs as appropriate. After the ligation reaction, the beads were immobilized and washed twice with 50 μL Wash Buffer. To release the ligated detectors from their RNA targets, the beads were resuspended in 30 μL and incubated for 5 min at 65° C. After incubation, the beads were immobilized, and the supernatant was removed and transferred to a storage plate.

For the optional amplification step, 5 μL of the supernatant, containing the ligation products, was transferred to a well of a PCR plate. Then 10 μL of a PCR cocktail was added, containing 0.45 U Taq polymerase, 0.6 μM P1 primer, 0.6 μM P2 primer, 1.5 mM $MgCl_2$, and 200 μM dNTPs. The thermocycler used the following program: 10 min at 94° C., followed by 20 to 25 cycles of 30 sec at 94° C., 30 sec at 58° C., and 30 sec at 72° C. The amplification products were then sequenced according to manufacturer's instructions. This representative ligation assay can be modified by the attenuators of the invention as in the following examples.

Example 2: Mutated Sequence Attenuators

In this experiment, the DD and/or UD were replaced with various attenuator oligos having one, two, or three mismatched bases. As discussed in Example 1, the DR' of the DD for GAPDH_2 had the sequence 5'-TGTAGCCAAAT-TCGTTGTCATACCA-3'(SEQ ID NO:3), so that the three nucleotides at the 3' terminus can be represented as -CCA-3'. The full sequence can be designated as the wildtype DD. Mutated versions of the DD were prepared, each having 3'-terminal sequences as follows (mutated bases shown in bolded lowercase):

| downstream attenuator | 3'-terminus | mutated positions |
|---|---|---|
| wildtype DD | -CCA | 0 |
| GAPDH_MM3_0b_D | -CCt | 1 |
| GAPDH_MM3_1b_D | -CgA | 1 |
| GAPDH_MM3_2b_D | -gCA | 1 |
| GAPDH_MM3_3b_D | -gCt | 2 |
| GAPDH_MM3_5b_D | -ggA | 2 |
| GAPDH_MM3_6b_D | -Cgt | 2 |
| GAPDH_MM3_4b_D | -ggt | 3 |

Similarly, the UR' of the UD had the sequence 5'-GGAAAT-GAGCTTGACAAAGTGGTCG-3' (SEQ ID NO:3), which can be designated as the wildtype UD, with a 5'-terminal sequence of /5Phos/GGA-. In this example, the sequence derived from the upstream regions remains underlined. Attenuator versions of the UD were prepared, each having 5'-terminal sequences:

| upstream attenuator | 5'-terminus | mutated positions |
|---|---|---|
| wildtype UD | /5Phos/GGA- | 0 |
| GAPDH_MM3_0b_U | /5Phos/cGA- | 1 |
| GAPDH_MM3_1b_U | /5Phos/GcA- | 1 |
| GAPDH_MM3_2b_U | /5Phos/GGt- | 1 |
| GAPDH_MM3_3b_U | /5Phos/cGt- | 2 |
| GAPDH_MM3_5b_U | /5Phos/Gct- | 2 |
| GAPDH_MM3_6b_U | /5Phos/ccA- | 2 |
| GAPDH_MM3_4b_U | /5Phos/cct- | 3 |

Combinations of the 8 DDs (wildtype and 7 mutated sequences) and 8 UDs (wildtype and 7 mutated sequences) were tested for attenuation of ligation in 64 experiments on RNA isolated from human kidney cell lines. As shown in FIG. 5, the positive control, using the wildtype DD and wildtype UD, correctly detected the presence of GAPDH_2 in the sample RNA by generating a species that joined DR' to UR', and specifically containing the following internal sequence at the ligation junction:

5'-CCAGGA-3' (SEQ ID NO: 6)

In each of the experiments, a DD and an UD were provided for a ligation experiment, and the ligation products were analyzed by sequencing and counting the number of reads containing DR' joined to UR', except with one of the 64 possible internal sequences formed by the junction. For example in one experiment, the ligation reaction was provided with downstream attenuator GAPDH_MM3_2b_D (or "2b_D") serving as the downstream detector for GAPDH_2, and upstream attenuator GAPDH_MM3_2b U ("2b_U") serving as the upstream detector for GAPDH_2. In the presence of GAPDH_2 sequence in the RNA sample, the pair of upstream and downstream attenuators generated a certain number of ligation products having the internal sequence 5'-gCAGGt-3'. (SEQ ID NO: 7)

The formation of these ligation products was sufficient to correctly detect the presence of GAPDH_2 in the samples, but at an attenuated level (33%) compared to the comparable experiment using wildtype detectors.

Greater attenuation was observed when using pairs of attenuators having more than one mutation. For example, the pairing of 5b_D and 3b_U yielded ligation products with the internal sequence 5'-ggAcGt-3', (SEQ ID NO: 14)

which resulted in detection of GAPDH_2, but at a much reduced level of only 0.58% of the positive control, representing an attenuation of 99.42%. No ligation products were detected when using the pair of 4b_U and 4b_U, with three mutations at each terminus. As disclosed herein, the degree of attenuation is not easily correlated with the number or position of mismatches. For example, the pairing of 0b_D and 0b_U yielded an attenuated level of 7.3%, which was ten-fold higher than most other combinations with similar attenuators. Nevertheless, when attenuation of a HAT such as GAPDH_2 is desired, the use of mismatched attenuators provides authentic detection of HATs without generating undesirable numbers of ligation product.

Example 3: Pattern Match Scores

The values shown in FIG. 5 provide the percent frequency of ligation in assays using downstream and upstream detector oligos with various patterns of matches (uppercase bases) and mismatches (lowercase bases) when hybridized to a template strand. The same values also indicate the frequency of ligation when combinations of downstream and upstream detectors are hybridized to a template having a different sequence, such as a similar full-length sequence (SFL).

FIG. 5b provides the ligation frequencies for the combinations of matches (I) and mismatches (X) in the form of match scores (MS) for a TSC's LSB with the DLSB and ULSB of an SFL:

| ligation frequency | MS |
|---|---|
| 0.00-0.22% | 0.9 highly selective |
| 0.22-0.50% | 0.7 |
| 0.50-20.00% | 0.4 |
| 20.00-100.00% | 0.1 poor selectivity |

The values in FIG. 5c follow a more stringent scoring for the frequencies in FIG. 5:

| 0.00-0.05% | 0.9 highly selective |
|---|---|
| 0.05-0.20% | 0.7 |
| 0.20-2.00% | 0.4 |
| 2.00-100.00% | 0.1 poor selectivity |

A scoring similar to FIG. 5b is provided in FIG. 5a, which incorporates ligation frequencies from additional HATs.

As a worked example, the topmost pair of hybridized sequences in FIG. 6 shows a 50-base TSC of CYP2C8:

5'-ACACAGGACCATAGACTTTTGAGAAATTGGTGAAAGATTTGCAGAT GTCC-3'

(residues 288 to 239 of SEQ ID NO:8), which is a member of the highly conserved cytochrome P450 family, having many highly homologous members and known roles in cancer formation and in the metabolism of anticancer drug metabolism. The downstream detector (DD) has a 25-base DR' (residues 288 to 264 of SEQ ID NO:8) and the upstream detector (UD) has the underlined 25-base UR' (residues 263 to 239 of SEQ ID NO:8). In this example, six ligation-selective bases are selected and are bolded GAA<u>ATT</u> (residues 266 to 261 of SEQ ID NO:8). Alternatively, FIG. 5a provides Match Scores when four LSBs are used (AA<u>AT</u>, residues 265 to 262 of SEQ ID NO:8) or two LSBs (A<u>A</u>), as well as asymmetrical LSBs such as GAA<u>AT</u> (residues 266 to 262 of SEQ ID NO:8) or AA<u>T</u>.

Based on a blastn search of the transcriptome for the TSC, the most similar full-length sequence (SFL) for the TSC is the mRNA of CYP2C18 (NM_000772.2), specifically the 50-base residues 519 to 470 of SEQ ID NO:18:

3'-uguguccсggυaucugaaaacucuuuaaccaauuccuaaacgagua cagg-5'

Based on the blastn search, these 50 bases of CYP2C18 align with the 25 bases of the DR' and the 25 bases of the UR' of CYP2C8 as shown, with only 5 mismatches. The aligned LSB are residues are 3'-cuuuaa-5' (residues 497 to 492 of CYP2C18). In this case, the LSB of the TSC (GAA <u>ATT</u>) is perfectly complimentary to the LSB of the SFL (cuuuaa). Six complementary bases are notated by the combination of -III and p-<u>III</u>- and the combination points to the upper right cell of FIG. 5a, which yields a Match Score of 0.1. The relatively low score (on a range from 0.0 to 1.0) indicates the detectors of this TSC would tend to hybridize to CYP2C18 and form a ligation product, thus yielding a false positive if performing the assay to detect the presence of CYP2C8.

FIG. 5a provides a set of Match Scores for each combination of 1, 2, and 3 downstream LSBs and 1, 2, and 3 upstream LSBs relative to a given similar full-length sequence. Detectors that have higher Match Scores (such as 0.9) tend to be the most selective for the target sequence of interest, even when in the presence of SFLs.

Example 4: Match Patterns

Continuing with CYP2C8 as a worked example, TSCs were identified that showed various match patterns. In FIG. 4a, the region of residues 1175 to 1121 contain an isolated mismatch when compared with the highly homologous mRNAs of CYP2C9, CYP2C18, and CYP2C19 (NM_000769.2) as SFLs. Six 50-base TSCs are shown in alignment with the SFLs to highlight the effect of the mismatches on the ligation-selective bases (TSB). In the first TSC (residues 1175 to 1126 of SEQ ID NO:8), the match pattern is IIII<u>IX</u>, for a match score of 0.1 using the matrix in FIG. 5a. When the 50-base TSC under consideration is shifted one base in the downstream direction (residues 1174 to 1125), the match pattern is III<u>IXI</u>, still a match score of 0.1 The match score improves when the TSC is shifted another base in the downstream direction: III<u>XII</u>, score=0.4. Further one-base shifts yield TSCs with match scores of 0.4, 0.4, and then 0.1. If this range of TSCs is considered for probe design, then the third and fourth TSCs in FIG. 4a would provide better selectivity (scores=0.4) against the SFLs.

FIG. 4b shows various TSCs that yield match pattern containing an XX, such as III<u>XXI</u> and IXX<u>III</u>, which have virtually perfect attenuation in FIG. 5, equivalent to high selectivity when applied to SFLs. When compared against the SFLs at the bottom, the TSCs have good (match score 0.4) to excellent (0.9) match scores that indicate higher selectivity against the SFLs.

FIG. 4c shows various TSCs with match patterns containing an XIX, such as III<u>XIX</u> and XIX<u>III</u>. FIG. 4d shows TSCs with excellent match patterns containing an XXXX or an XIXIX against the SFLs. FIG. 4e shows a series of TSCs where residues 513 to 454 of CYP2C8 are perfectly complementary to SFL CYP2C19, save two pairs of mismatches. Based on sequence complementarity alone, these TSC probes will all hybridize well to CYP2C19 mRNAs present in a sample. The TSCs are not all equal as probes in a ligation assay. By shifting the TSCs one base at a time, however, the match patterns deliver exquisite prioritization of the TSCs from 0.1 to 0.9 to 0.1 as the Castor-and-Pollux mismatches complete their transit across the LSB window.

Example 5: Probe Design Pipeline

The 1924-base mRNA sequence of CYP2C8 (NM_000770) was selected as a representative example. A set of 188 target sequence candidates (TSCs) were selected as 50-base subsequences of CYP2C8, starting at the 5'-end of the sequence and walking 10 bases downstream for each TSC. Thus, the first TSC (TSC1) was residues 50 to 1 (3'-5'), TSC2 was residues 60 to 11, TSC3 was residues 71 to 21, and so on until TSC 188 (residues 1920 to 1871).

A nucleotide blast (blastn) search was performed for each TSC against the entire human Reference RNA sequence (NM) database, hosted by NCBI, to represent the human transcriptome. The default search parameters were used, although a number of algorithm parameters were used, such as setting the Expect Threshold to 0.1. Other parameter settings include match=2, mismatch=−3, gap open=−5, and gap extension=−1. The RNA sequence (NM) having the most similarity to each TSC was noted and aligned to the TSC.

For each TSC and aligned SFL, a Match Score was determined based on the match patterns in FIG. 5a. As illustrated in FIG. 2, for example, TSC 13 (residues 170 to 121 of SEQ ID NO:8) had a match pattern against SFL CYP2C18 mRNA of XXXIXI. This pattern yielded a match score of 0.9—a highly selective TSC. The SFL for TSC 37 (residues 410 to 361 of SEQ ID NO:8) was also CYP2C18 mRNA with a match pattern of IXXIII, which yielded a match score of 0.1—a poorly selective TSC. The SFL for TSC 95 (residues 990 to 941), TSC 151 (1550 to 1501), and TSC 182 (1860 to 1811) was CYP2C19 mRNA (NM_000769), with match patterns of IXXXII, XXIXII, and IIIIII. Accordingly, the TSCs would have a match score of 0.9 (highly selective), 0.9 (highly selective), and 0.1 (poor selectivity). It bears repeating that each TSC is perfectly complementary to its native sequence (here, CYP2C8 mRNA) and will produce a ligation product (a true positive). However, candidate TSCs may cross-react with highly related RNA sequences in the sample, such as CYP2C9 and CYP2C19 mRNAs. The match score provides a measure of the selectivity of the TSC against false positives to related off-target sequences: detector oligos based on CYP2C8 TSC 151 (MS 0.9) will generate ligation products based on the presence of CYP2C8 mRNA (true positive), but will not generate ligation product based on the presence of any other known RNA sequence in the transcriptome. By contrast, CYP2C8 detector oligos based on TSC 182 (MS 0.1) are more likely to generate ligation product in the presence of both CYP2C8 mRNA (true positive) and CYP2C19 mRNA (off-target false positive).

As an optional step to enhance the selection of TSCs with highest selectivity, a match score of 1.0 was assigned to the few CYP2C8 TSCs that yielded no similar match at all during the blastn search under the parameters used. Such was the case for TSCs 26, 27, 30, 31, 32, 33, 34, 38, 29, 40, 41, and 150. If found, these matchless TSCs were preferred for the full-length target sequence of interest to make probes, unless other considerations weighed against them.

As another optional step, it was recognized that some full-length target sequences were sufficiently related to the full-length sequence of interest that should be considered a cluster of related sequences (isoforms), as shown in FIG. 2. For example, NM_000770.3 (SEQ ID NO:8) was the first CYP2C8 sequence described. Subsequent splice variants were described: variant 2 (NM_001198853.1), variant 2 (NM_001198854.1), and variant 3 (NM_001198855.1). For purposes of this example, the four variants of CYP2C8 were considered as a cluster. When the blastn search was performed for each TSC, the other members of the cluster were excluded from being considered an SFL in generating the match scores. In the case measurement of these specific variants is desired, then rather than designing the DD and UD's to measure all the isoforms, LSBs could be used to differentially measure each isoform.

Several other considerations discussed herein were used to prioritize the selection of TSCs to design detector oligos. Out of the 188 TSCs, three were selected for further consideration of probe synthesis: TSC 32 (residues 360 to 311 of SEQ ID NO:8), TSC 34 (residues 380 to 331), and TSC 39 (430 to 381).

The process described above for CYP2C8 (and its isoforms) was repeated for approximately 23,000 mRNAs in the NCBI database, generating highly selective detector oligo designs for synthesis that significantly reduced the likelihood of false positives arising from even the most similar potential sequences in the sample.

Example 6: Comparison with TSC Designs for Splice Junctions and % GC Content

Previous methods for ligation assays have considered TSCs of various lengths and selected them based on factors such as the location of splice junctions and the % GC (guanine and cytosine) content of the probes. As a comparison, five TSCs that spanned exon junctions of CYP2C8 were considered under the parameters of the invention. As shown in FIG. 6, the TSCs were aligned by a blastn search with their respective SFLs CYP2C18 and CYP2C19. The first TSC (residues 288 to 239 of SEQ ID NO:8) yielded a match pattern of IIIIII and a match score of 0.1, indicating that detector oligos based on the TSC would hybridize well to CYP2C18 and likely result in ligation products that were false-positive. This was true for the other four exon junction TSCs.

The % GC content of detector oligos was also considered, as used in prior methods. FIG. 7a shows a profile of the TSCs for CYP2C8 ranked by desirable % GC, which offers scant guidance for the selection of a selective TSC.

For the five TSCs, % GC content would indicate that TSCs spanning exon junctions a|b, c|d, and d|e are excellent for probe design. However, determination of their match scores provided herein indicate that use of these probes in ligation assays would result in numerous false positives. For comparison, FIG. 7c presents a profile of the TSCs according to the factors provided herein.

Skilled artisans will appreciate that additional embodiments are within the scope of the invention. The invention is defined only by the following claims, and limitations from the specification or its examples should not be imported into the claims.

The invention claimed is:

1. A method for selectively detecting target nucleic acid sequences of a plurality of full-length sequences of interest (FLSs) in a sample, wherein the FLSs are members of a defined set of full-length species that may be present in the sample, comprising the steps of
(a) selecting a target sequence for each FLS by
(1) defining a plurality of subsequences of the FLS as target sequence candidates (TSCs),
wherein each TSC has a downstream region (DR) and an upstream region (UR),
wherein the DR has ligation-selective bases (DLSB) at the 5'-end, or the UR has ligation-selective bases (ULSB) at the 3'-end, or both, collectively being the ligation-selective bases (TSC-LSB);
(2) identifying a similar full-length species (SFL) in the defined set that comprises regions that are similar to regions in the TSC, wherein the SFL has ligation-selective bases (SFL-LSB) that correspond to the ligation-selective bases of the target sequence candidate (TSC-LSB);
(3) selecting a TSC to be the target sequence based on the following factors:
(i) the difference of one or more bases of the TSC-LSB to the corresponding bases of the SFL-LSB;
(b) contacting the sample with pairs of target sequence oligos, each pair comprising
(1) a downstream detector oligo (DD) comprising a portion (DR') complementary to the DR of the selected TSC, and
(2) an upstream detector oligo (UD) comprising a portion (UR') complementary to the UR of the selected TSC;
(c) ligating the DD and UD if both are hybridized to the DR and UR of a target sequence in the sample;
whereby the ligation product indicates detection of the target sequence that is selective over SFLs in the sample.

2. The method of claim 1, wherein the defined set of full-length species is the human transcriptome.

3. The method of claim 2, wherein the defined set has at least 500 species.

4. The method of claim 1, wherein the number of target nucleic acid sequences is at least 500.

5. The method of claim 1, wherein the TSC is at least 20 bases in length.

6. The method of claim 1, wherein the TSC-LSB is at least 2 or more bases in length.

7. The method of claim 1, wherein a TSC is preferentially selected that is dissimilar from all other sequences in the defined set.

8. The method of claim 7, wherein the dissimilarity is determined by a blastn comparison.

9. The method of claim 1, wherein the degree of similarity in step (a)(3)(i) is based on a predetermined set of values for patterns of complementary bases.

10. The method of claim 1, wherein a factor of step (a)(3) is
(ii) penalizing a TSC if the 25th base in the 5'-to-3' direction is a C.

11. The method of claim 1, wherein a factor of step (a)(3) is
(ii) penalizing a TSC for distance from the 3'-end of the FLS.

12. The method of claim 1, wherein a cluster of isoforms is identified from members of the defined set that share a common sequence, and the defined set excludes the isoforms of the cluster.

13. The method of claim 12, wherein the FLS is the longest isoform of the cluster.

14. The method of claim 12, wherein a factor of step (a)(3) is
(ii) penalizing a TSC for being present in fewer than all the isoforms of the cluster.

15. The method of claim 1, wherein a factor of step (a)(3) is
(ii) penalizing a TSC if a detector oligo has a homopolymeric run of 2 or more bases.

16. The method of claim 1, wherein a factor of step (a)(3) is
(ii) penalizing a TSC if a detector oligo has more than 2 repeated dinucleotides.

17. The method of claim 1, wherein a factor of step (a)(3) is
(ii) penalizing a TSC if the GC % of a detector oligo is less than 40% or greater than 60%.

18. The method of claim 1, wherein the DR and UR are separated by at least one nucleotide, and the method further comprises (b1) extending the DR' using the sample as template.

19. The method of claim 1, wherein the sample is provided in liquid phase.

20. The method of claim 1, wherein the sample is provided attached to a solid substrate.

21. The method of claim 20, wherein the sample is formalin-fixed paraffin-embedded (FFPE) tissue or cells.

22. The method of claim 20, wherein steps (b) and (c) are performed on the sample in situ.

* * * * *